United States Patent
Bagaoisan et al.

(10) Patent No.: US 11,707,266 B2
(45) Date of Patent: *Jul. 25, 2023

(54) APPARATUS AND METHODS FOR SEALING A VASCULAR PUNCTURE

(71) Applicant: ACCESS CLOSURE, INC., Santa Clara, CA (US)

(72) Inventors: Celso J. Bagaoisan, Union City, CA (US); Juan Domingo, Union City, CA (US); Sieu Duong, San Francisco, CA (US)

(73) Assignee: ACCESS CLOSURE, INC., Santa Clara, CA (US)

( * ) Notice: Subject to any disclaimer, the term of this patent is extended or adjusted under 35 U.S.C. 154(b) by 16 days.

This patent is subject to a terminal disclaimer.

(21) Appl. No.: 17/021,969

(22) Filed: Sep. 15, 2020

(65) Prior Publication Data

US 2021/0169458 A1 Jun. 10, 2021

(51) Int. Cl.
*A61B 17/00* (2006.01)

(52) U.S. Cl.
CPC .. *A61B 17/0057* (2013.01); *A61B 2017/0065* (2013.01); *A61B 2017/00654* (2013.01)

(58) Field of Classification Search
CPC ........ A61B 17/0057; A61B 2017/0065; A61B 2017/00654; A61B 2017/00893; A61B 2017/00898; A61B 2090/034; A61B 2090/0811
See application file for complete search history.

(56) References Cited

U.S. PATENT DOCUMENTS

| | | |
|---|---|---|
| 2,365,039 A | 12/1944 | Andresen |
| 3,765,419 A | 10/1973 | Usher |
| 4,002,173 A | 1/1977 | Manning et al. |
| 4,472,542 A | 9/1984 | Nambu |
| 4,655,211 A | 4/1987 | Sakamoto et al. |
| 4,664,857 A | 5/1987 | Nambu |
| 4,734,097 A | 3/1988 | Tanabe et al. |
| 4,738,658 A | 4/1988 | Magro et al. |

(Continued)

FOREIGN PATENT DOCUMENTS

| | | |
|---|---|---|
| EP | 0476178 A1 | 3/1992 |
| WO | 9222252 A1 | 12/1992 |

(Continued)

OTHER PUBLICATIONS

Chisholm R.A., et al., "Fibrin Sealant as a Plug for the Post Liver Biopsy Needle Track," Clinical Radiology, 1989, vol. 40 (6), pp. 627-628.

(Continued)

*Primary Examiner* — Mohamed G Gabr
(74) *Attorney, Agent, or Firm* — ArentFox Schiff LLP

(57) ABSTRACT

An apparatus for sealing a puncture includes a cartridge, a pusher member, a sealant, and a tamping device on a proximal end of the cartridge. During use, the cartridge, sealant, and pusher member are advanced over a positioning member and into the puncture by advancing a cartridge hub carrying the tamping device. When further distal advancement of the cartridge is limited, the cartridge hub is further advanced, activating the tamping device, and causing the pusher member to advance relative to the sealant to compress the sealant within the puncture.

12 Claims, 23 Drawing Sheets

(56) References Cited

U.S. PATENT DOCUMENTS

| | | |
|---|---|---|
| 4,790,819 A | 12/1988 | Li et al. |
| 4,838,280 A | 6/1989 | Haaga |
| 4,852,568 A | 8/1989 | Kensey |
| 4,890,612 A | 1/1990 | Kensey |
| 5,012,059 A | 6/1991 | Kensey |
| 5,061,274 A | 10/1991 | Kensey |
| 5,108,421 A | 4/1992 | Fowler |
| 5,192,302 A | 3/1993 | Kensey |
| 5,221,259 A | 6/1993 | Weldon et al. |
| 5,228,851 A | 7/1993 | Burton |
| 5,258,042 A | 11/1993 | Mehta |
| 5,275,616 A | 1/1994 | Fowler |
| 5,290,310 A | 3/1994 | Makower |
| 5,292,332 A | 3/1994 | Lee |
| 5,310,407 A | 5/1994 | Casale |
| 5,320,639 A | 6/1994 | Rudnick |
| 5,324,306 A | 6/1994 | Makower et al. |
| 5,334,216 A | 8/1994 | Vidal et al. |
| 5,370,660 A | 12/1994 | Weinstein et al. |
| 5,383,896 A | 1/1995 | Gershony et al. |
| 5,431,639 A | 1/1995 | Shaw |
| 5,391,183 A | 2/1995 | Janzen et al. |
| 5,409,703 A | 4/1995 | McAnalley et al. |
| 5,411,520 A | 5/1995 | Nash et al. |
| 5,413,571 A | 5/1995 | Katsaros et al. |
| 5,419,765 A | 5/1995 | Weldon et al. |
| 5,437,292 A | 8/1995 | Kipshidze et al. |
| 5,437,631 A | 8/1995 | Jansen |
| 5,441,517 A | 8/1995 | Kensey et al. |
| 5,464,396 A | 11/1995 | Barta et al. |
| 5,486,195 A | 1/1996 | Myers et al. |
| 5,514,158 A | 5/1996 | Kanesaka |
| 5,529,577 A | 6/1996 | Hammerslag |
| 5,542,949 A | 8/1996 | Yoon |
| 5,550,187 A | 8/1996 | Rhee et al. |
| 5,571,181 A | 11/1996 | Li |
| 5,580,923 A | 12/1996 | Yeung et al. |
| 5,591,205 A | 1/1997 | Fowler |
| 5,643,464 A | 1/1997 | Rhee et al. |
| 5,601,602 A | 2/1997 | Fowler |
| 5,626,601 A | 5/1997 | Gershony et al. |
| 5,700,477 A | 12/1997 | Rosenthal et al. |
| 5,782,860 A | 1/1998 | Epstein et al. |
| 5,716,375 A | 2/1998 | Fowler |
| 5,718,916 A | 2/1998 | Scherr |
| 5,725,498 A | 3/1998 | Jansen et al. |
| 5,725,551 A | 3/1998 | Myers et al. |
| 5,744,153 A | 4/1998 | Yewey et al. |
| 5,752,974 A | 5/1998 | Rhee et al. |
| 5,780,044 A | 7/1998 | Yewey et al. |
| 5,836,970 A | 11/1998 | Pandit |
| 5,868,778 A | 2/1999 | Gershony et al. |
| 5,916,236 A | 6/1999 | Muijs et al. |
| 5,928,266 A | 7/1999 | Kontos |
| 5,948,429 A | 9/1999 | Bell et al. |
| 5,948,829 A | 9/1999 | Wallajapet et al. |
| 5,951,583 A | 9/1999 | Jensen et al. |
| 5,957,952 A | 9/1999 | Gershony et al. |
| 5,972,375 A | 10/1999 | Truter et al. |
| 5,973,014 A | 10/1999 | Funk et al. |
| 6,017,359 A | 1/2000 | Gershony et al. |
| 6,022,361 A | 2/2000 | Epstein et al. |
| 6,048,358 A | 4/2000 | Barak |
| 6,051,248 A | 4/2000 | Sawhney et al. |
| 6,056,768 A | 5/2000 | Cates et al. |
| 6,056,769 A | 5/2000 | Epstein et al. |
| 6,063,061 A | 5/2000 | Wallace et al. |
| 6,083,522 A | 7/2000 | Chu et al. |
| 6,152,943 A | 11/2000 | Sawhney |
| 6,162,240 A | 12/2000 | Cates et al. |
| 6,162,241 A | 12/2000 | Coury et al. |
| 6,165,201 A | 12/2000 | Sawhney et al. |
| 6,179,862 B1 | 1/2001 | Sawhney |
| 6,179,863 B1 | 1/2001 | Kensey et al. |
| 6,238,412 B1 | 5/2001 | Dubrul et al. |
| 6,262,059 B1 | 7/2001 | Pamukcu et al. |
| 6,271,278 B1 | 8/2001 | Park et al. |
| 6,287,323 B1 | 9/2001 | Hammerslag |
| 6,302,898 B1 | 10/2001 | Edwards et al. |
| 6,325,789 B1 | 12/2001 | Janzen et al. |
| 6,350,274 B1 | 2/2002 | Li |
| 6,371,975 B2 | 4/2002 | Cruise et al. |
| 6,379,373 B1 | 4/2002 | Sawhney et al. |
| 6,458,147 B1 | 10/2002 | Cruise et al. |
| 6,475,177 B1 | 11/2002 | Suzuki |
| 6,482,179 B1 | 11/2002 | Chu et al. |
| 6,514,534 B1 | 2/2003 | Sawhney |
| 6,566,406 B1 | 5/2003 | Pathak et al. |
| 6,569,185 B2 | 5/2003 | Ungs |
| 6,605,294 B2 | 8/2003 | Sawhney |
| 6,608,117 B1 | 8/2003 | Gvozdic |
| 6,610,026 B2 | 8/2003 | Cragg et al. |
| 6,613,070 B2 | 9/2003 | Redmond et al. |
| 6,626,861 B1 | 9/2003 | Hart et al. |
| 6,635,068 B1 | 10/2003 | Dubrul et al. |
| 6,689,148 B2 | 2/2004 | Sawhney et al. |
| 6,699,261 B1 | 3/2004 | Cates et al. |
| 6,703,047 B2 | 3/2004 | Sawhney et al. |
| 6,774,151 B2 | 8/2004 | Malmgren et al. |
| 6,780,197 B2 | 8/2004 | Roe et al. |
| 6,818,008 B1 | 11/2004 | Cates et al. |
| 6,818,018 B1 | 11/2004 | Sawhney |
| 6,860,895 B1 | 3/2005 | Akerfeldt et al. |
| 6,863,924 B2 | 3/2005 | Ranganathan et al. |
| 6,887,974 B2 | 5/2005 | Pathak |
| 6,890,343 B2 | 5/2005 | Ginn et al. |
| 6,960,617 B2 | 11/2005 | Omidian et al. |
| 6,964,658 B2 | 11/2005 | Ashby et al. |
| 7,009,034 B2 | 3/2006 | Pathak et al. |
| 7,316,704 B2 | 1/2008 | Bagaoisan et al. |
| 7,331,979 B2 | 2/2008 | Khosravi et al. |
| 7,331,981 B2 | 2/2008 | Cates et al. |
| 7,335,220 B2 | 2/2008 | Khosravi et al. |
| 7,553,319 B2 | 6/2009 | Bagaoisan et al. |
| 7,611,479 B2 | 11/2009 | Cragg et al. |
| 7,621,936 B2 | 11/2009 | Cragg et al. |
| 7,790,192 B2 | 9/2010 | Khosravi et al. |
| 7,803,172 B2 | 9/2010 | Khosravi et al. |
| 7,806,856 B2 | 10/2010 | Bagaoisan et al. |
| 7,824,414 B2 | 11/2010 | Evans |
| 7,850,710 B2 | 12/2010 | Huss |
| 7,955,353 B1 | 6/2011 | Ashby et al. |
| 8,088,144 B2 | 1/2012 | Ginn et al. |
| 8,128,654 B2 | 3/2012 | Khosravi et al. |
| 8,262,693 B2 | 9/2012 | Pai et al. |
| 8,382,797 B2 | 2/2013 | Khosravi et al. |
| 8,382,798 B2 | 2/2013 | Khosravi et al. |
| 8,394,122 B2 | 3/2013 | Bagaoisan et al. |
| 8,617,204 B2 | 12/2013 | Khosravi et al. |
| 9,713,462 B2 * | 7/2017 | Bagaoisan ......... A61B 17/0057 |
| 2001/0031948 A1 | 10/2001 | Cruise et al. |
| 2001/0046518 A1 | 11/2001 | Sawhney |
| 2001/0047187 A1 | 11/2001 | Milo et al. |
| 2001/0051813 A1 | 12/2001 | Hnojewyj |
| 2002/0062104 A1 | 5/2002 | Ashby et al. |
| 2002/0072767 A1 | 6/2002 | Zhu et al. |
| 2002/0106409 A1 | 8/2002 | Sawhney et al. |
| 2002/0188319 A1 | 12/2002 | Morris et al. |
| 2003/0012734 A1 | 1/2003 | Pathak et al. |
| 2003/0078616 A1 | 4/2003 | Ginn et al. |
| 2003/0088271 A1 | 5/2003 | Cragg et al. |
| 2004/0176798 A1 | 9/2004 | Epstein et al. |
| 2004/0204741 A1 | 10/2004 | Egnelov et al. |
| 2004/0249342 A1 | 12/2004 | Khosravi et al. |
| 2004/0267193 A1 | 12/2004 | Bagaoisan et al. |
| 2004/0267307 A1 | 12/2004 | Bagaoisan et al. |
| 2004/0267308 A1 * | 12/2004 | Bagaoisan ......... A61B 17/0057 606/213 |
| 2005/0085773 A1 | 4/2005 | Forsberg |
| 2005/0267522 A1 | 12/2005 | Yassinzadeh et al. |
| 2005/0277980 A1 | 12/2005 | Yassinzadeh |
| 2006/0034930 A1 * | 2/2006 | Khosravi ......... A61L 26/0052 424/484 |
| 2006/0099238 A1 | 5/2006 | Khosravi et al. |

(56) References Cited

U.S. PATENT DOCUMENTS

| | | |
|---|---|---|
| 2006/0100664 A1 | 5/2006 | Pai et al. |
| 2006/0229673 A1 | 10/2006 | Forsberg |
| 2006/0229674 A1 | 10/2006 | Forsberg |
| 2006/0253072 A1 | 11/2006 | Pai et al. |
| 2006/0265006 A1 | 11/2006 | White et al. |
| 2007/0032823 A1 | 2/2007 | Tegg |
| 2007/0032824 A1 | 2/2007 | Terwey |
| 2007/0123817 A1 | 5/2007 | Khosravi et al. |
| 2007/0135837 A1 | 6/2007 | Yassinzadeh |
| 2007/0231366 A1 | 10/2007 | Sawhney et al. |
| 2007/0255314 A1 | 11/2007 | Forsber et al. |
| 2008/0009794 A1 | 1/2008 | Bagaoisan et al. |
| 2008/0058862 A1 | 3/2008 | Khosravi et al. |
| 2008/0082122 A1 | 4/2008 | Khosravi et al. |
| 2008/0161849 A1 | 7/2008 | Cates et al. |
| 2008/0243182 A1 | 10/2008 | Bates et al. |
| 2009/0088793 A1 | 4/2009 | Bagaoisan et al. |
| 2009/0143817 A1 | 6/2009 | Akerfeldt et al. |
| 2009/0254110 A1 | 10/2009 | Bagaoisan et al. |
| 2010/0211000 A1 | 8/2010 | Killion et al. |
| 2014/0214075 A1 | 7/2014 | Khosravi et al. |

FOREIGN PATENT DOCUMENTS

| | | |
|---|---|---|
| WO | 9838920 A1 | 9/1998 |
| WO | 9922646 A1 | 5/1999 |
| WO | 0014155 A1 | 3/2000 |
| WO | 0019912 A1 | 4/2000 |
| WO | 03015840 A2 | 2/2003 |
| WO | 03094749 A1 | 11/2003 |
| WO | 2004093690 A1 | 11/2004 |
| WO | 2006052611 A1 | 5/2006 |
| WO | 2008033964 A2 | 3/2008 |

OTHER PUBLICATIONS

Clayman R.V., et al., "Renal Vascular Complications Associated with the Percutaneous Removal of Renal Calculi," The Journal of Urology, 1984, vol. 132, pp. 228-230.

Extended European Search Report for European Application No. 15190309, dated Feb. 11, 2016, 6 pages.

Feliciano., "Abstract: Use of Balloon Catheter Tamponade in Vascular Wounds," The Journal of Trauma, 1984, vol. N (7), p. 657.

Feliciano D.V., et al., "Balloon Catheter Tamponade in Cardiovascular Wounds," The American Journal of Surgery, 1990, vol. 160 (6), pp. 583-587.

Gazelle G.S., et al., "Hemostatic Protein-polymer Sheath: New Method to Enhance Hemostasis at Percutaneous Biopsy," Radiology, 1990, vol. 175 (3), pp. 671-674.

Gross, "A Manual of Military Surgery," ChapterV: Wounds and other injuries,1861, pp. 45-73.

International Search Report for Application No. PCT/US2009/064272, dated Apr. 29, 2010, 7 pages.

Kaye K.W., et al., "Tamponade Nephrostomy Catheter for Percutaneous Nephrostolithotomy," Urology, 1986, vol. 275), pp. 441-445.

MedGadget, New Angio-Seal Evolution Goes to Market, Oct. 17, 2008, Retrieved from http://www.medgadget. t;com/2008/10/new_vascular_closure_device_goes_to_market.html, 2 pages.

Non-Final Office Action dated Sep. 1, 2015 for U.S. Appl. No. 13/774,607, 10 pages.

Non-Final Office Action dated Jul. 15, 2015 for U.S. Appl. No. 14/094,145, 6 pages.

Pfab et al., "Animal Experiments on Hemostasis with a Collagen-Fibrin Tissue-Adhesive Sealant in the Nephrostomy Tract," Urology International, 1987, vol. 42, pp. 207-209.

Pfab et al., "Local Hemostasis of Nephrostomy Tract with Fibrin Adhesive Sealing in Percutaneous Nephrolithotomy," European Urology,1987, vol. 13, pp. 118-121.

Riley, et al., "Percutaneous Liver Biopsy with Plugging of Needle Track: A Safe Method for Use in Patients with Impaired Coagulation," The Lancet, 1984, p. 436.

Smiley, et al., "Balloon Catheter Tamponade of Major Vascular Wounds," The American Journal ofSurgery, 1971, vol. 121, pp. 326-327.

St. Jude's Angie-Seal Evolution Vascular Closure Device gets FDA and European CE Mark approval-Update, Oct. 4, 2008, Retrieved from the Internet URL: http://www.rttnews.com/740734/st-jude-s-angio-seal-evolution-vascular-evice-gets-fda-and-european-ce-mark-approval-update.aspx, 2 pages.

St. Jude Medical, Angio-Seal Evolution Vascular Closure Device, Instructions for Use, 2008. 12 pages.

Takayasu K., et al., "A New Hemostatic Procedure for Percutaneous Transhepatic Portal Vein Catheterization," Japanese Journal of Clinical Oncology, 1988, vol. 18 (3), pp. 227-230.

The International Bureau of WIPO, International Search Report and Written Opinion for international Application No. PCT/US2007/078328; dated Jul. 7, 2008, 15 pages.

\* cited by examiner

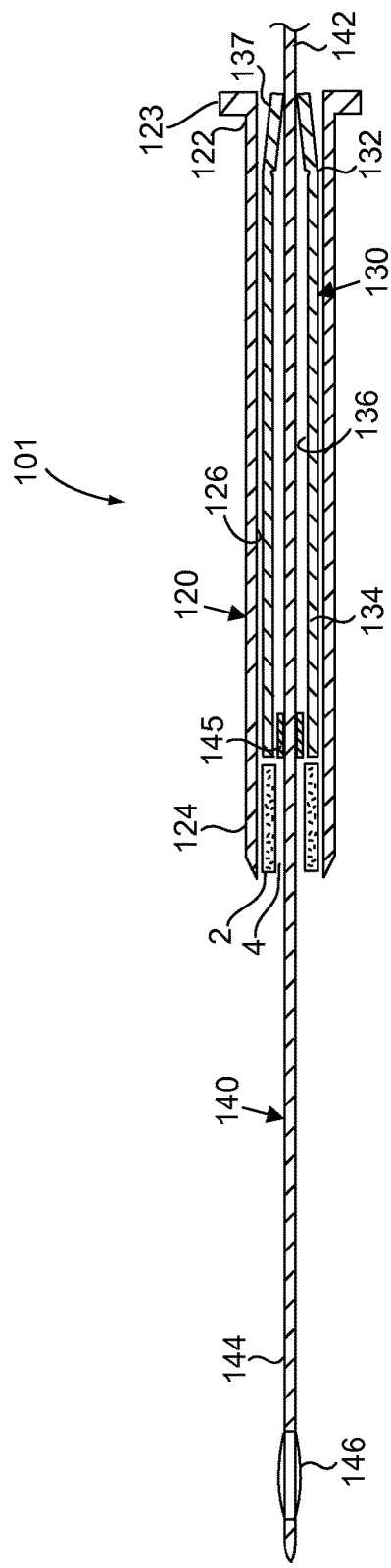
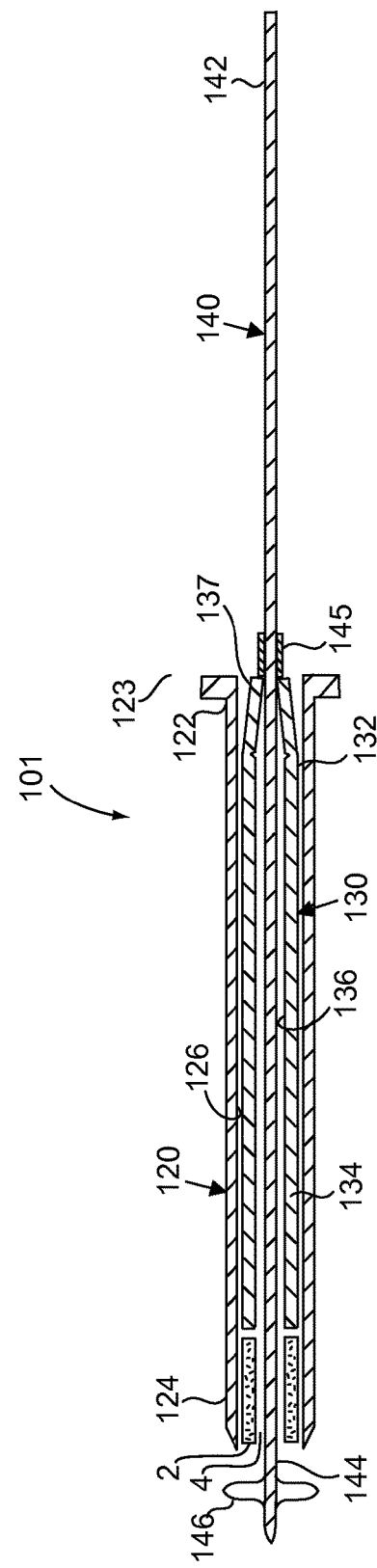
FIG. 2A
FIG. 2B

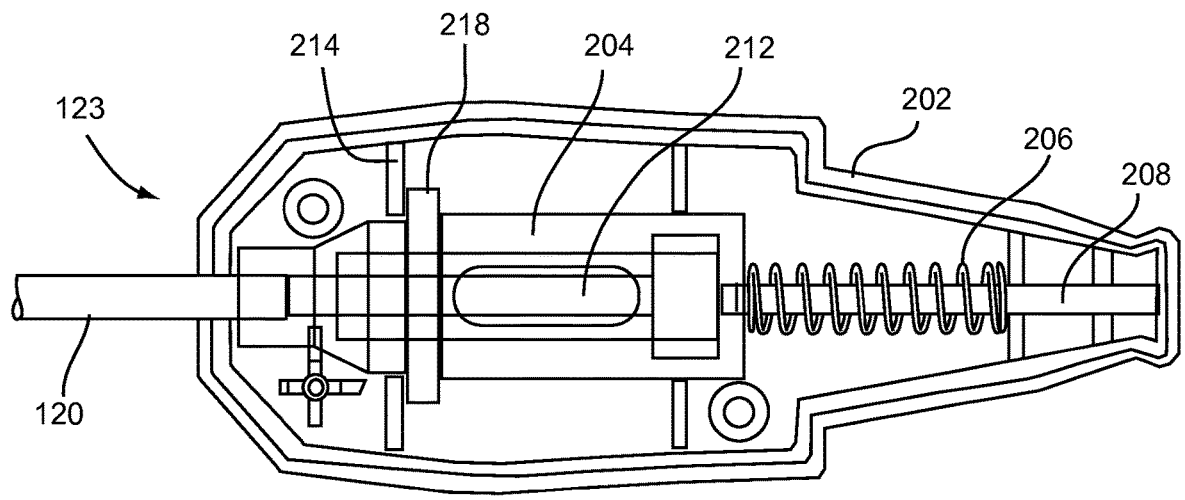
FIG. 3A(1)
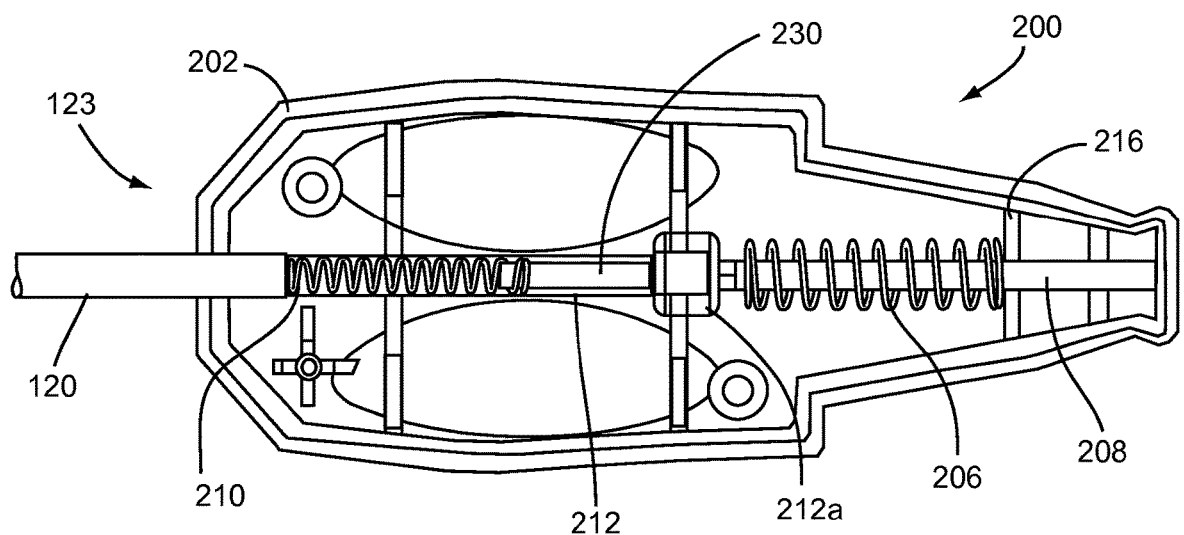
FIG. 3A(2)

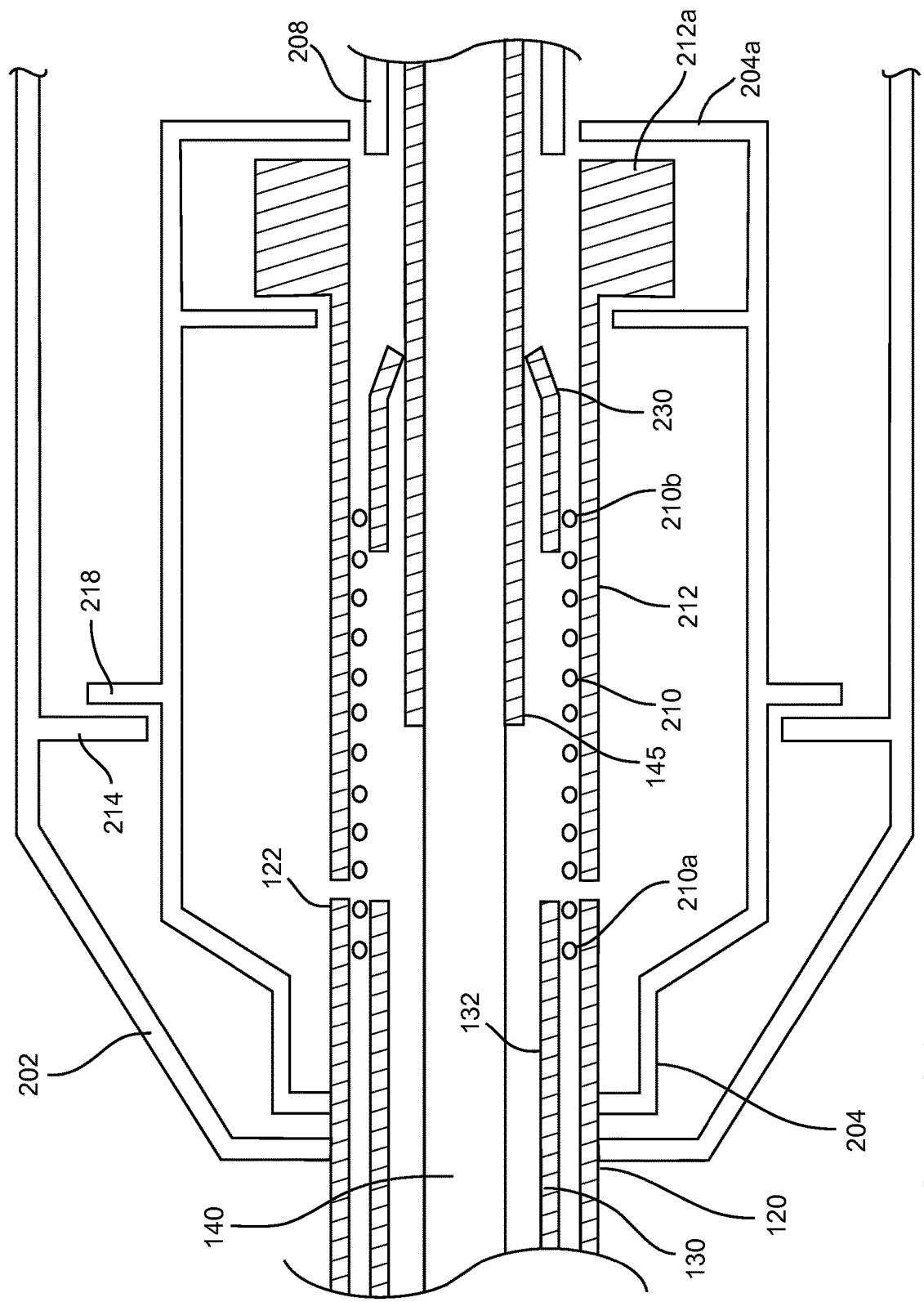
FIG. 3A(3)

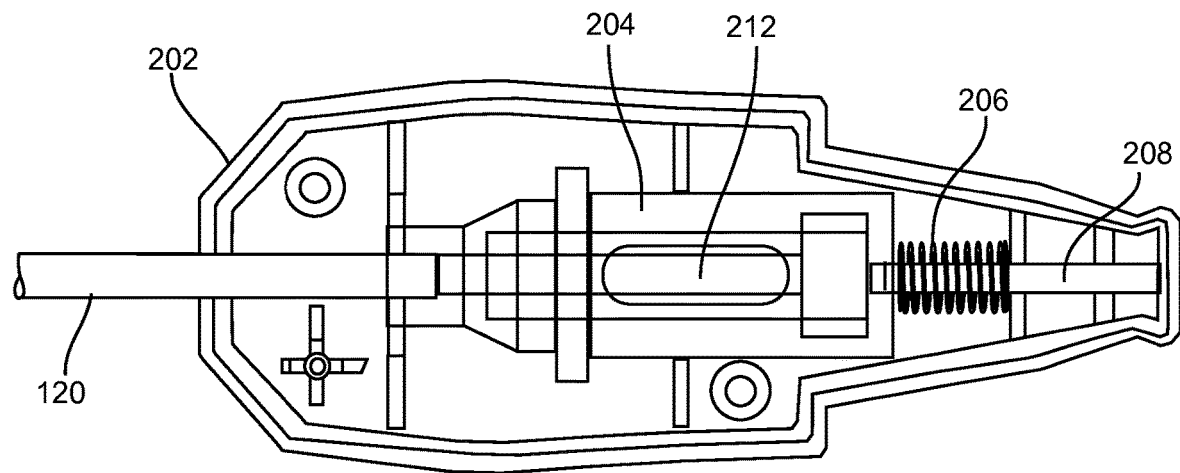
FIG. 3B(1)
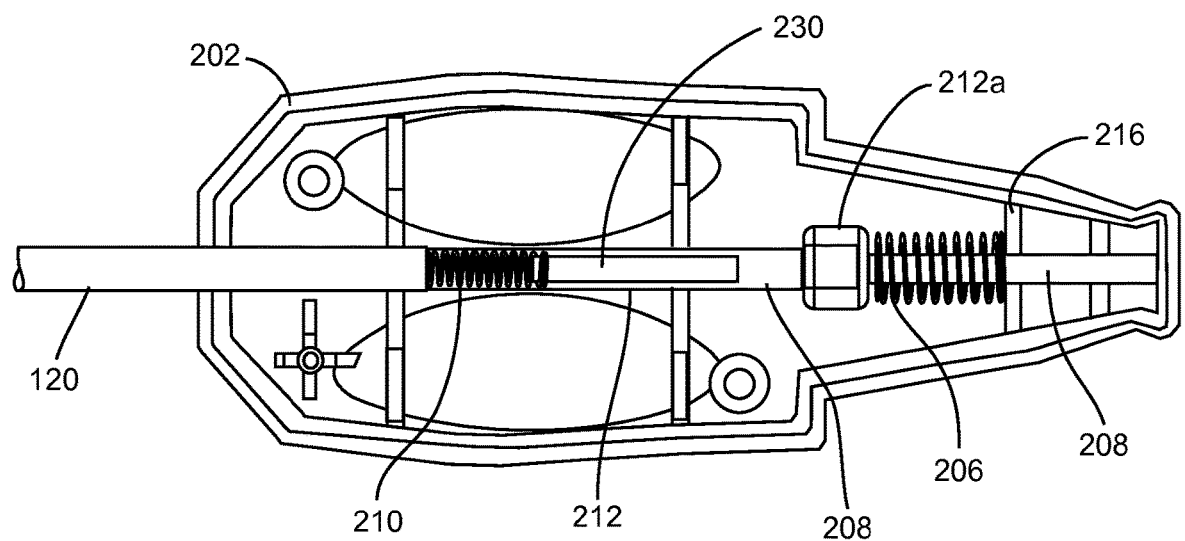
FIG. 3B(2)

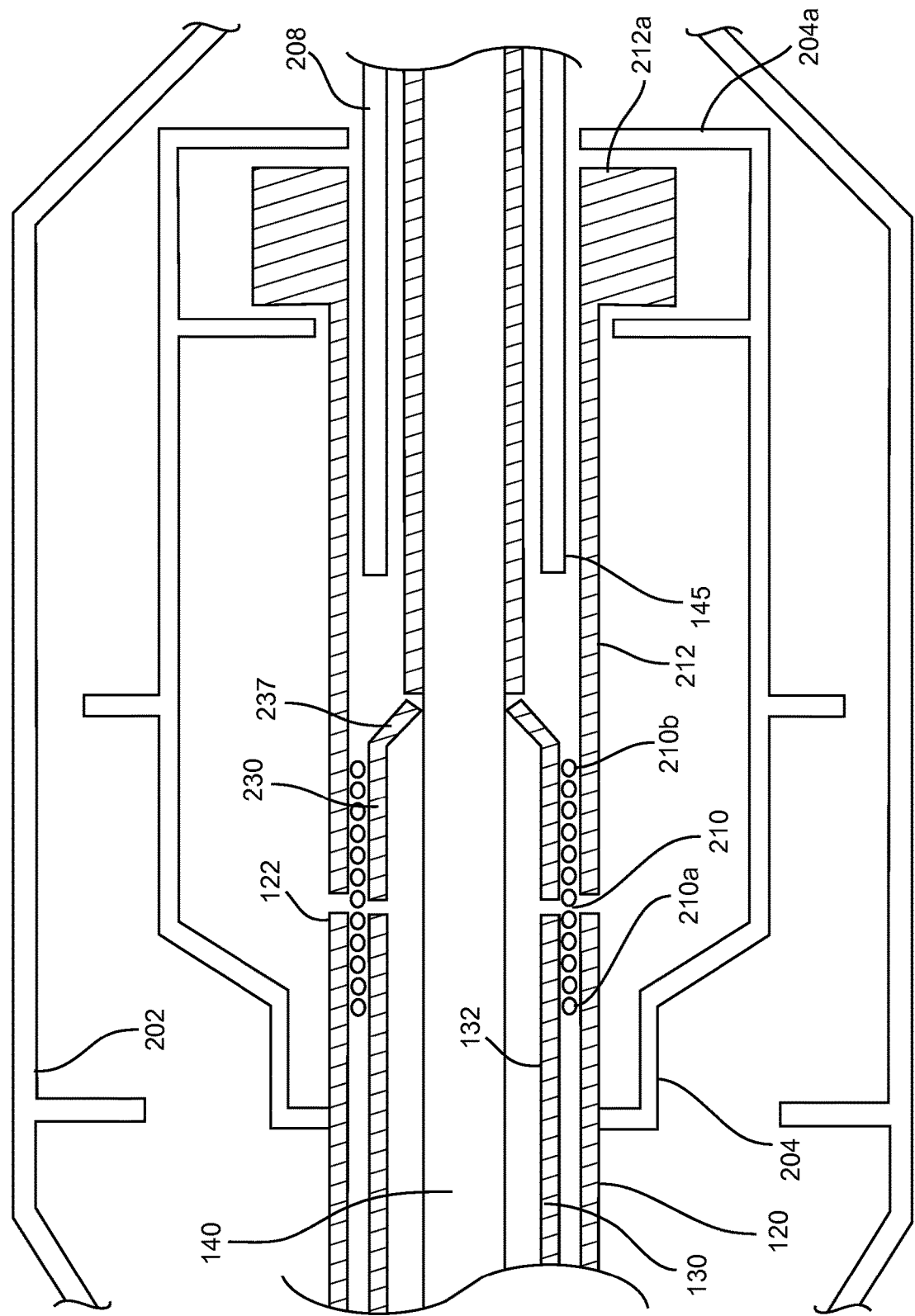
FIG. 3B(3)

APPARATUS AND METHODS FOR SEALING A VASCULAR PUNCTURE

RELATED APPLICATION DATA

This application is a continuation of U.S. patent application Ser. No. 15/633,093 filed on Jun. 26, 2017, now U.S. Pat. No. 10,806,438 issued on Oct. 20, 2020, which is a divisional of U.S. patent application Ser. No. 13/774,607 filed on Feb. 22, 2013, now U.S. Pat. No. 9,713,462 issued on Jul. 25, 2017, which is a continuation of U.S. patent application Ser. No. 12/617,693 filed on Nov. 12, 2009, now U.S. Pat. No. 8,394,122 issued on Mar. 12, 2013, which claims benefit of U.S. provisional patent application Ser. No. 61/114,049 filed on Nov. 12, 2008, the entire disclosures of each of the foregoing being hereby expressly incorporated herein by reference.

FIELD OF THE INVENTION

The present invention relates generally to apparatus and methods for sealing punctures in a body, and more particularly, to apparatus and methods for sealing a vascular puncture extending through tissue into a blood vessel, and to apparatus and methods for delivering a plug, sealant, and/or other material into a percutaneous puncture extending from a patient's skin to a blood vessel or other body lumen, e.g., to seal the puncture.

BACKGROUND

Apparatus and methods are known for accessing a patient's vasculature percutaneously, e.g., to perform a procedure within the vasculature, and for sealing the puncture that results after completing the procedure. For example, a hollow needle may be inserted through a patient's skin and overlying tissue into a blood vessel. A guide wire may be passed through the needle lumen into the blood vessel, whereupon the needle may be removed. An introducer sheath may then be advanced over the guide wire into the vessel, e.g., in conjunction with or subsequent to one or more dilators.

A catheter or other device may be advanced through the introducer sheath and over the guide wire into a position for performing a medical procedure. Thus, the introducer sheath may facilitate accessing and/or introducing various devices into the vessel, while minimizing trauma to the vessel wall and/or minimizing blood loss. Upon completing the procedure, the device(s) and introducer sheath may be removed, leaving a puncture extending between the skin and the vessel wall.

To seal the puncture, external pressure may be applied to the overlying tissue, e.g., manually and/or using sandbags, until hemostasis occurs. This procedure, however, may be time consuming and expensive, requiring as much as an hour of a medical professional's time. It is also uncomfortable for the patient, and may require the patient to remain immobilized in the operating room, catheter lab, or holding area. In addition, a risk of hematoma exists from bleeding before hemostasis occurs.

SUMMARY

The present invention is directed to apparatus and methods for sealing a puncture in a body, and, more particularly, to apparatus and methods for providing temporary or permanent hemostasis within a vascular puncture extending into a blood vessel, and/or to apparatus and methods for delivering a sealant and/or other material into a percutaneous puncture extending from a patient's skin to a blood vessel or other body lumen.

In accordance with one embodiment, an apparatus is provided for sealing a puncture extending through tissue that includes an elongate member including a proximal end, a distal end sized for insertion into a puncture through tissue, and an expandable member on the distal end. The apparatus also includes a cartridge including a proximal end, a distal end sized for insertion into the puncture, and a lumen extending between the proximal and distal ends sized for receiving the elongate member therein, a sealant disposed within the cartridge lumen adjacent the cartridge distal end, a pusher member disposed within the cartridge lumen adjacent to the sealant, and a tamping or auto advance device on the cartridge proximal end for biasing the pusher member distally relative to the sealant when activated.

In accordance with another embodiment, an apparatus is provided for sealing a puncture extending through tissue. The apparatus may include an elongate member, a cartridge, a sealant disposed within the cartridge, a pusher member disposed within the cartridge adjacent to the sealant, and an auto advance device. The sealant may be positioned adjacent to a distal end of the cartridge and the auto advance device may be positioned on a proximal end of the cartridge. The elongate member may optionally include a marker for indicating when the auto advance device is in an active position.

In one embodiment, the auto advance device may include a cartridge hub and a slider tube. The slider tube may be fixed to the cartridge proximal end and may be slidable relative to the cartridge hub. The auto advance device may further include a tamping spring and an auto advance spring. The tamping spring may be positioned between the pusher member and a secondary pusher member and, optionally, may be compressible between the pusher member and the secondary pusher member. The elongate member may include an element for engaging with a latch element on the secondary pusher member. The auto advance spring may be compressible between the slider tube and an inner surface of the cartridge hub.

In another embodiment, the auto advance device may include a spring for distally advancing the pusher member, thereby compressing the sealant between the pusher member and an expandable member on a distal end of the elongate member.

In accordance with yet another embodiment, a tamping apparatus is provided for tamping a sealant delivered within a puncture. The tamping apparatus may include a housing, a slider tube, an auto advance spring, a tamping spring, and an auto advance spring tube. The slider tube is disposed within the housing and may be slidable relative to the housing between an inactive position and an active position. In the inactive position, the tamping spring and the auto advance spring may be extended. In the active position, the tamping spring and the auto advance spring may be compressed. The auto advance spring may be compressible between the slider tube and a proximal rib of the housing and may surround the auto advance spring tube. The tamping spring may be disposed within the slider tube and coupled between a pusher tube and a secondary pusher tube. The apparatus may further include a tamping tube within the slider tube, and the tamping spring may be disposed within the tamping tube. The auto advance spring tube may be configured to protrude into the slider tube, thereby distally advancing the secondary pusher tube and compressing the tamping spring. The secondary pusher tube may include a latch element for engaging with a raised element on an elongate positioning member.

In accordance with still another embodiment, a method is provided for sealing a puncture extending through tissue to a body lumen. The method may include advancing a positioning member through the puncture until an expandable element thereon is disposed within the body lumen, expanding the expandable element within the body lumen, and retracting the positioning member until the expanded expandable element contacts a wall of the body lumen adjacent the puncture. A cartridge, carrying a sealant, a pusher member, and a proximal cartridge hub, may be advanced into the puncture, e.g., over the positioning member until a distal end of the cartridge contacts the expandable element and/or an auto advance device in the cartridge hub is activated. The cartridge may be withdrawn from the puncture while maintaining the sealant and the pusher member within the puncture, and the auto advance device may automatically compress the sealant within the puncture, e.g., between the pusher member and the expandable element.

In one embodiment, the cartridge hub may be advanced until a distal end of the cartridge contacts the expandable element, and then the cartridge hub may be advanced further to activate the auto advance device. For example, the auto advance device may include one or more biasing elements, e.g., a tamping spring and an auto advance spring, that may be compressed when the cartridge hub is advanced. The tamping spring may be positioned between a pusher member and a secondary pusher member and a latch element on the secondary pusher member may engage with an element on the positioning member during further advancing of the cartridge hub. Withdrawing the cartridge may expand the auto advance spring while the tamping spring may remain compressed. Tamping the sealant may include expanding a tamping spring, thereby advancing the pusher member further into the puncture and compressing the sealant between the expandable member and the pusher member.

In one embodiment, the method may further include collapsing the expandable element and removing the positioning member from the puncture, thereby withdrawing the collapsed expandable element through the sealant. The positioning member may optionally include a marker thereon and further advancing the cartridge hub may include advancing the cartridge hub until a cartridge hub proximal end passes the marker, e.g., to provide a visual indicator that the cartridge hub has been advanced sufficiently to activate the auto advance device.

In accordance with yet another embodiment, a tamping mechanism is provided that includes a middle hub, a housing, a spring biased so a distal end of the spring displaces a tamping device in a distal direction, a latch coupled to the housing for engaging with a latching detent on the middle hub in one latch position and for engaging with the tamping device in another latch position, and a pusher member slidably disposed within a proximal end of the middle hub, a proximal end of the pusher member for engaging with the tamping device. The pusher member may be movable distally to tamp a sealant when the tamping device is released by the latch. The tamping mechanism may further include a spring clip for biasing the latch in the another latch position.

In accordance with still another embodiment, a tamping mechanism is provided that includes a middle hub, a housing, a spring biased so a distal end of the spring displaces a tamping device in a distal direction, a trigger pin slidably disposed within the housing, and a pusher member slidably disposed within a proximal end of the middle hub. A proximal end of the pusher member may engage with the tamping device. The pusher member may be movable distally to tamp a sealant when the tamping device is released. The trigger pin may be moveable proximally upon engagement with the middle hub, thereby releasing a stopper plate. In one embodiment, the tamping device includes a leaf spring for displacing the stopper plate in a position enabling distal movement of the tamping device. In another embodiment, the tamping device includes a spring biased hub latch for displacing the stopper plate in a position enabling distal movement of the tamping device.

In accordance with yet another embodiment, a method is provided for sealing a puncture extending through tissue to a body lumen. The method may include advancing a positioning member through the puncture until an expandable element thereon is disposed within the body lumen, expanding the expandable element within the body lumen, and retracting the positioning member until the expanded positioning element contacts a wall of the body lumen adjacent the puncture.

A cartridge, carrying a sealant, a pusher member, and a proximal cartridge hub, may be advanced into the puncture until a distal end of the cartridge contacts the expandable element and/or an auto advance device in the cartridge hub is activated, e.g., by compressing a tamping spring and an auto advance spring in the auto advance device. The cartridge may be withdrawn from the puncture while maintaining the sealant and the pusher member within the puncture, and the sealant may be compressed within the puncture, e.g., between the pusher member and the expandable element, by the auto advance device, e.g., by expanding the tamping spring.

In accordance with still another embodiment, a method is provided for sealing a puncture extending through tissue to a body lumen. The method may include advancing a positioning member through the puncture until an expandable element thereon is disposed within the body lumen, expanding the expandable element within the body lumen, and retracting the positioning member until the expanded positioning element contacts a wall of the body lumen adjacent the puncture.

A cartridge, carrying a sealant and a pusher member, may be advanced into the puncture until a distal end of the cartridge contacts the expandable element and the pusher member is compressed between a catch on the positioning member and the sealant. An auto advance device on the cartridge is then activated, thereby allowing the compressed pusher member to expand axially and compress the sealant between the pusher member and the expandable element. For example, the pusher member may include a tamping spring and the tamping spring may be compressed, thereby shortening the pusher member, yet biasing the pusher member to extend axially.

The cartridge may be withdrawn, leaving the sealant and pusher member within the puncture. The expandable element may be collapsed and the positioning member withdrawn, e.g., through the sealant and pusher member, whereupon the pusher member may be removed.

Other aspects and features of the present invention will become apparent from consideration of the following description taken in conjunction with the accompanying drawings.

BRIEF DESCRIPTION OF THE DRAWINGS

FIGS. 2A and 2B are cross-sectional views of a distal portion of the apparatus of FIGS. 1A and 1B, with the cartridge in proximal and distal positions, respectively.

FIGS. 3A(1)-3A(3) are cross-sectional views of a hub of the cartridge of FIG. 1A showing components of an auto advance device therein in an inactive position.

FIGS. 3B(1)-3B(3) are cross-sectional views of a hub of the cartridge of FIG. 1A showing components of the auto advance device of FIGS. 3A(1)-3A(3) in an active position.

DETAILED DESCRIPTION OF THE EXEMPLARY EMBODIMENTS

Figure 1A:
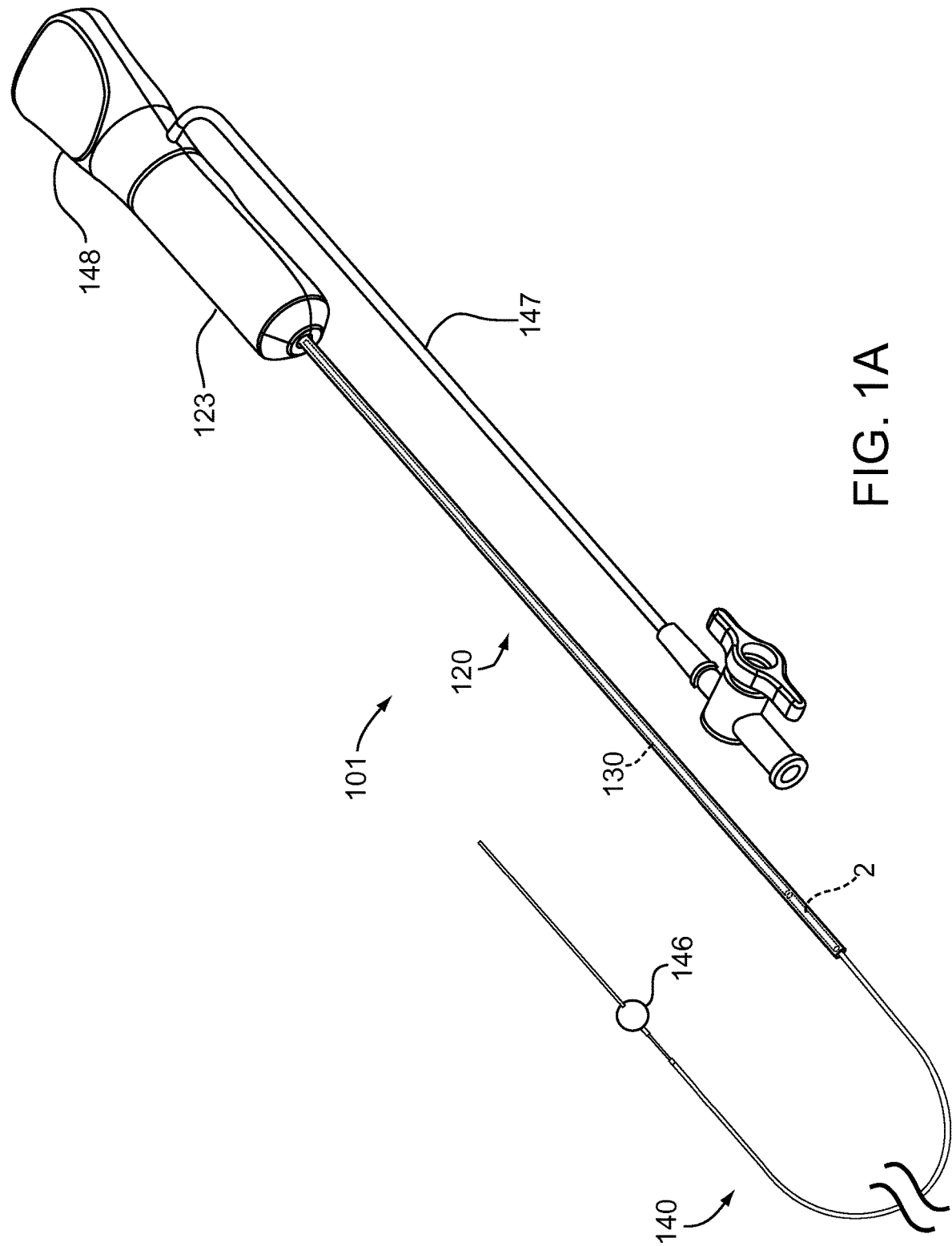
FIG. 1A is a perspective view of an exemplary embodiment of an apparatus for delivering a sealant into a puncture through tissue, including a cartridge carrying the sealant and a positioning member.
Figure 1B:
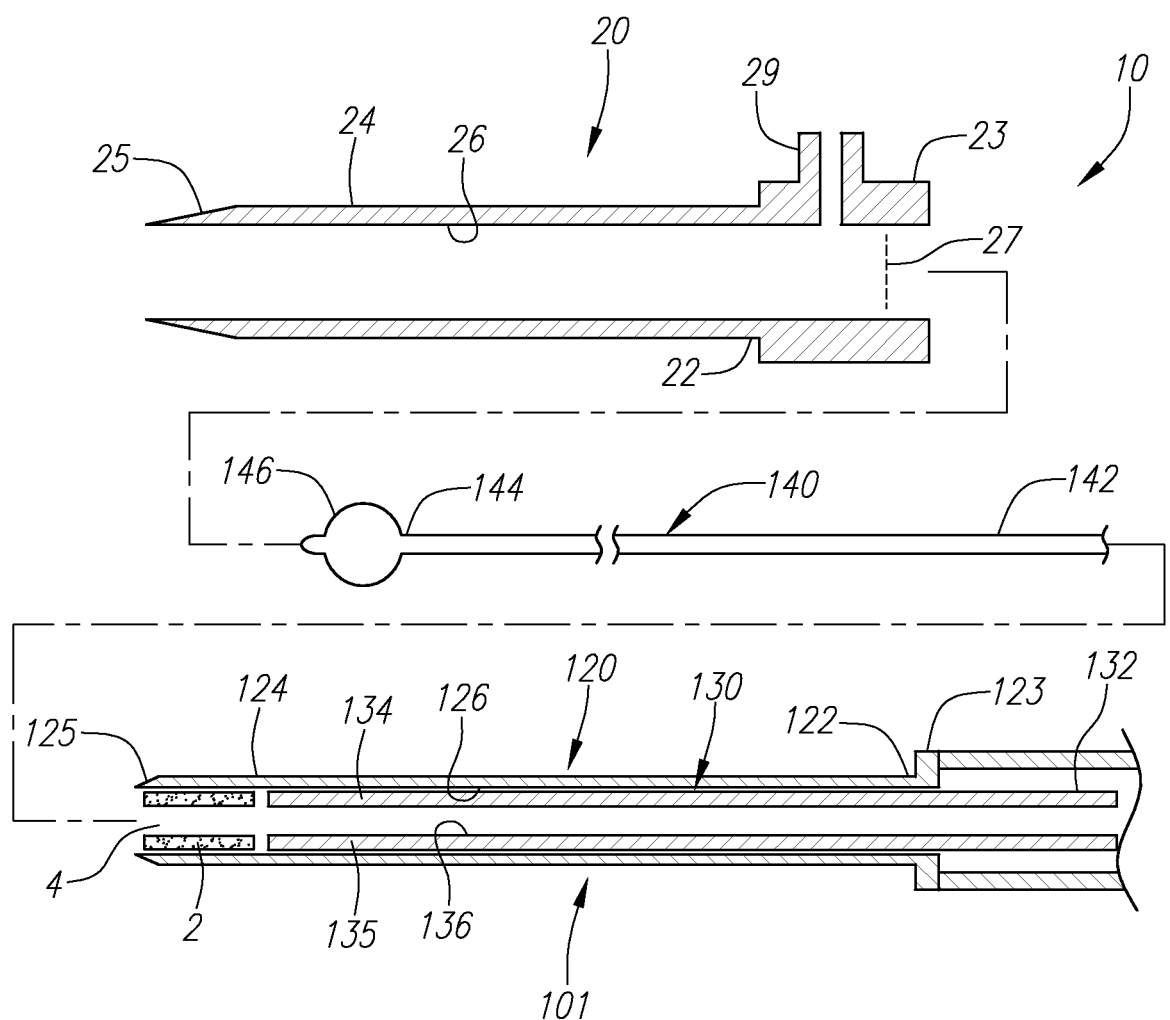
FIG. 1B is an exploded cross-sectional side view of a system for delivering a sealant into a puncture through tissue, including the apparatus of FIG. 1A and an introducer sheath.

Turning to the drawings, FIGS. 1A and 1B show an exemplary embodiment of an apparatus 101 and a system 10, respectively, for sealing a puncture through tissue. Generally, as shown in FIG. 1A, the apparatus 101 includes a cartridge or other tubular member 120, and a positioning or occlusion member 140 including a positioning member housing 148. As best seen in FIG. 1A, the cartridge 120 includes a sealant 2 therein, a plunger, tamping member, advancing member, or other pusher member 130 carried by the cartridge 120, and a cartridge hub 123. As shown in FIG. 1B, the apparatus 101 may be part of a system 10, e.g., which may also include a delivery, access, procedure, introducer, or other sheath 20. Optionally, the system 10 may include one or more other components, e.g., a needle, guidewire, and/or other instrument(s) for creating a puncture, a syringe or other source of inflation media and/or vacuum, and/or a source of additional sealing compound (not shown).

As best seen in FIG. 1B, the introducer sheath 20 may be a generally tubular body including a proximal end 22, a distal end 24 sized for insertion into a puncture through tissue, and a lumen 26 extending between the proximal and distal ends 22 and 24. The introducer sheath 20 may be formed from a substantially rigid, semi-rigid, and/or flexible tubular body including a hub 23 on the proximal end 22. The introducer sheath 20 may have sufficient length to extend from a patient's skin through any intervening tissue into a blood vessel or other body lumen, e.g., having a length between about ten centimeters and twenty centimeters (10-20 cm), and may have an outer diameter between about 1.6 millimeters and four millimeters (1.6-4 mm). The distal end 24 may be tapered and/or may include a substantially atraumatic distal tip 25 for facilitating advancement through tissue and/or a puncture.

The introducer sheath 20 may be formed using known materials and/or methods, e.g., plastic with the tubular body and hub 23 substantially permanently connected together, e.g., using one or more of an interference fit, one or more mating connectors (not shown), bonding with adhesive, sonic welding, and the like. The hub 23 generally includes one or more seals (not shown) adjacent an opening 27, which may prevent flow of blood or other fluids out of the hub 23 from the lumen 26, yet accommodate insertion of one or more instruments into the lumen 26, such as the cartridge 120 and/or positioning member 140. Optionally, as shown, the hub 23 may include a side port 29 communicating with the lumen 26, e.g., for coupling a source of saline or other fluid (not shown) to the hub 23.

With additional reference to FIG. 1B, the cartridge 120 is generally an elongate tubular body including a proximal end 122, a distal end 124 sized for introduction into the lumen 26 of the introducer sheath 20, and a lumen 126 extending between the proximal and distal ends 122, 124. The cartridge 120 may be substantially rigid, semi-rigid, or flexible, e.g., such that the cartridge 120 may be advanced through the introducer sheath 20 or otherwise into a puncture through tissue. The cartridge 120 may also include a tapered and/or substantially atraumatic distal tip 125 and/or an enlarged handle or hub 123 on the proximal end 122. In one embodiment, the hub 123 includes a tamping or auto-advance device, as discussed in more detail below.

Optionally, the system 10 may include a locking member (not shown) for coupling the introducer sheath 20 to the cartridge 120 during use such that subsequent movement of the cartridge 120, e.g., proximally during retraction, causes the introducer sheath 20 to be pulled or otherwise moved along with the cartridge 120. This coupling may prevent accidental proximal movement of the cartridge 120 independent of the introducer sheath 20, which may otherwise result in deploying the sealant 2 from the cartridge 120 within the introducer sheath 20, rather than within a puncture itself. Exemplary embodiments of locking elements that may be used are disclosed in co-pending U.S. patent application Ser. No. 11/864,835, filed Sep. 28, 2007, and published as U.S. Publication No. 2009/0088793, the entire disclosure of which is hereby expressly incorporated by reference.

The sealant 2 is provided within the distal portion of the cartridge 120 and the pusher member 130 is provided proximal to the sealant 2 within the cartridge 120. The sealant 2 may include a biocompatible, bioabsorbable, and/or expandable material, such as a freeze-dried hydrogel. The sealant 2 may have a solid or hollow cylindrical shape, a rolled sheet shape, a disk shape, or other shapes or cross-sections, such as elliptical, triangular, square, conical, disk, or polygonal shapes. For example, the sealant 2 may be formed from a solid material including a lumen 4 extending between proximal and distal ends thereof, as shown in FIG. 1B. The lumen 4 may be created by rolling a sheet of material around a mandrel, by molding, by boring into, or otherwise removing material from an already formed solid material, and the like. The lumen 4 may be dimensioned such that the positioning member 140, a guidewire, and/or other instruments (not shown) may slide or otherwise pass through the sealant 2, as described elsewhere herein.

The sealant 2 may be substantially homogeneous or may include one or more different materials at one or more locations. For example, in one embodiment, the sealant 2 may include a carrier or core having first and second hydrogel precursors disposed thereon in an unreactive state, which may provide a "sticky" adherent coating when the sealant 2 is exposed to an aqueous environment. In one embodiment, the sealant 2 may be formed from a biocompatible and/or bioabsorbable hydrogel, e.g., polyethylene glycol ("PEG"), or other synthetic material. For example, the hydrogel may include a lyophilized (i.e., freeze-dried) PEG polymer that includes hydrolytically degradable chemical groups, e.g., including a macroporous polymer network, which may uptake fluid and expand when exposed to an aqueous environment. The magnitude of expansion or swelling (pre to post hydration) may be significant, e.g., between about two and ten times (2X-10X) its lyophilized size based on volume.

In addition or alternatively, the sealant 2 may include pro-thrombotic material, e.g., including one or more biological pro-thrombotics, such as collagen, fibrin, carboxymethylcellulose, oxidized cellulose, alginates, gelatin, or other protein-based material, and/or synthetic materials, such as polyglycolic acids (PGA's), polyactides (PLA's), polyvinyl alcohol, and the like. Optionally, the sealant 2 may include one or more therapeutic and/or pharmaceutical agents, e.g., to promote healing, prevent infection, and/or other adverse medical events, and the like. Such agents may be embedded in the sealant material and/or applied as one or more coatings or layers. Exemplary materials and methods for making and using them are disclosed in U.S. Pat. Nos. 6,152,943, 6,165,201, 6,179,862, 6,514,534, 6,379,373, 6,703,047, 7,009,034, 6,887,974, and in co-pending U.S. patent application Ser. No. 10/454,362, filed Jun. 4, 2003, published as US 2004/0249342, Ser. No. 10/982,387, filed Nov. 5, 2004, published as US 2006/0034930, Ser. No. 10/982,384, filed Nov. 5, 2004, published as US 2006/0099238, and Ser. No. 11/465,791, filed Aug. 18, 2006 published as US 2007/0231366. The disclosures of these references are expressly incorporated by reference herein.

The sealant 2 may be disposed within the lumen 126 of the cartridge 120 proximate to the distal end 124, e.g., immediately adjacent the distal tip 125. Thus, when advanced into the introducer sheath 20 or otherwise within the puncture, the sealant 2 may remain out of direct or indirect contact with blood or other bodily fluids along the blood path. Optionally, the cartridge 120 may include a split distal end (not shown), e.g., formed by creating one or more relatively short longitudinal cuts or slots extending proximally from the distal end 124. The split distal end may facilitate retraction of the cartridge 120 relative to the sealant 2, e.g., by providing extra flexibility at the distal end 124. Such cuts or slots may allow the distal end 124 to separate more easily from the sealant 2, e.g., as the sealant begins to expand upon being exposed to an aqueous environment, such as blood or other bodily fluids. The lumen 126 may be sized such that the cartridge 120 and sealant 2 are slidable relative to one another, e.g., to allow the cartridge 120 to be retracted proximally relative to the sealant 2 and/or pusher member 130.

With further reference to FIG. 1B, the pusher member 130 may be an elongate tubular body, e.g., a plunger or catheter, including a proximal end 132, a distal end 134 sized for introduction into the lumen 126 of the cartridge 120, and a lumen 136 extending between the proximal and distal ends 132, 134. The pusher member 130 may be sized for being slidably received within the lumen 126 of the cartridge 120, although the pusher member 130 may abut or otherwise interact with the hub 123 of the cartridge 120 such that the pusher member 130 is advanced distally when the cartridge 120 is advanced distally. The distal end 134 of the pusher member 130 may terminate in a substantially blunt distal tip 135, e.g., to facilitate contacting, pushing, advancing, tamping, and/or "cinching" the sealant 2 within a puncture, as described further below. In one embodiment, the proximal end 132 of the pusher member 130 interacts with an auto-advance device in the hub 123, as discussed in more detail below.

The pusher member 130 may be substantially rigid, semi-rigid, and/or substantially flexible, having sufficient column strength to allow proximal movement of the cartridge 120 relative to the sealant 2 without buckling the pusher member 130 and/or to allow the distal tip 135 of the pusher member 130 to be "tamped" down on sealant 2 within a puncture, e.g., by pushing from the proximal end 132, as described elsewhere herein. The lumen 136 of the pusher member 130 may be sized to accommodate the positioning member 140, a guidewire (not shown), a flowable sealing compound, and/or fluid therethrough. As explained elsewhere herein, the pusher member 130 may include an axially compressible or foreshortenable portion, e.g., that may be compressed, yet is biased to extend axially towards its original length. For example, a tamping spring 210 may be provided adjacent the proximal end 132 of the pusher member 130, e.g., between the proximal end 132 and a secondary pusher member 230.

Alternatively, the tamping spring 210 may be coupled to and extend from the proximal end 132 of the pusher member 130 without the secondary pusher member 230. The tamping spring 210 may be compressed by an auto advance device 200 (not shown, see FIGS. 3A-3B) within the hub 123 during use, thereby biasing the distal end 134 of the pusher member 130 to move distally, as explained further below.

With continued reference to FIGS. 1A and 1B, the positioning member 140 generally is an elongate member including a proximal end 142, a distal end 144, a positioning or occlusion element 146 on the distal end 144, and a housing 148 on the proximal end 142. The positioning element 146 may be an expandable member, such as a balloon, a wire mesh structure, an expandable frame, and the like. The positioning element 146 may be selectively expandable, e.g., using a source of inflation media, a pull wire, and/or other actuator (not shown), operable from the proximal end 142 of the positioning member 140.

For example, as shown in FIGS. 1A and 1B, the positioning element may be a balloon 146, and the positioning member 140 may be a tubular body including a lumen (not shown) extending between the proximal and distal ends 142, 144 and communicating with an interior of the balloon 146. For example, a syringe 149 (not shown, see FIGS. 4A, 5A, 6A) may communicate with the housing 148 (and consequently the lumen and interior of the balloon 146) via tubing 147 connected to a port on the housing 148. Optionally, the positioning member 140 may include an internal pull wire and piston arrangement (not shown) that causes the balloon 146 to shorten during expansion and extend during collapse. Exemplary embodiments of positioning members 140 including balloons that may be used are disclosed in co-pending U.S. patent application Ser. No. 10/454,362, filed Jun. 4, 2003, published as US 2004/0249342, Ser. No. 11/112,877, filed Apr. 22, 2005, published as US 2006/0253072, and Ser. No. 11/112,971, filed Apr. 22, 2005, and published as US 2008/0009794. The entire disclosures of these references are expressly incorporated by reference herein.

Alternatively, the positioning element 146 may be biased to an enlarged condition, but may be compressed to a contracted condition, e.g., by an overlying sleeve or other constraint (not shown). The constraint may be removed to expose the positioning element, allowing the expandable element to automatically expand to the enlarged condition. Additional information on expandable structures that may be provided on the positioning member 140 may be found in U.S. Pat. Nos. 6,238,412, 6,635,068, and 6,890,343. The entire disclosures of these references are expressly incorporated herein by reference.

Optionally, the positioning member 140 may include a transition cuff (not shown) on the distal end 144 adjacent and distal to the positioning element 146. The transition cuff may comprise a flexible material similar to the structure of material used in the positioning element 146, e.g., as described elsewhere herein. The transition cuff may provide the apparatus 101 with a seal to minimize exposure of the sealant 2 to fluids during introduction and/or may provide an atraumatic tip to lessen injury to the vessel during initial insertion of the apparatus 101 into the puncture and vessel. During expansion of the positioning element 146, the transition cuff may be displaced off the distal end of the positioning element 146 and fold adjacent to the positioning element 146. A lubricious coating may be applied to the transition cuff and/or positioning element 146 to ease the folding of the transition cuff during the expansion of the positioning element 146. Additional information on transition cuffs and systems and methods including them may be found in co-pending application Ser. No. 11/854,534, filed Sep. 12, 2007, published as U.S. Publication No. 2008/0082122, the entire disclosure of which is expressly incorporated by reference herein.

Turning to FIGS. 2A and 2B, the apparatus 101 may be used to position and deliver the sealant 2 within a puncture, e.g., extra-vascularly just above or otherwise adjacent to an arteriotomy in a blood vessel or other body lumen communicating with a puncture, as described further elsewhere herein. In one embodiment, as shown in FIG. 2A, the cartridge 120 (along with the pusher member 130 and sealant 2) may be initially provided on the proximal end 142 of the positioning member 140. For example, the housing 148 (not shown in FIGS. 2A and 2B, see FIG. 1A) on the positioning member 140 and the hub 123 on the cartridge 120 may be initially connected to one another, e.g., using one or more releasable detents (not shown) and the like. The cartridge 120 may be slidable distally along the positioning member 140, e.g., by disconnecting the hub 123 from the housing 148, and then advancing the hub 123 and the cartridge 120 until the distal end 124 of the cartridge 120 is disposed adjacent the positioning element 146, as shown in FIG. 2B. For example, the detents may simply separate from one another when the hub 123 is advanced away from the housing 148 with sufficient force. Alternatively, one of the hub 123 and housing 148 may include an actuator or lock (not shown) that may be activated to separate the detents and/or otherwise allow the cartridge 120 to be advanced relative to the positioning member 140. Alternatively, the cartridge 120 and pusher member 130 may be initially provided adjacent the distal end 144 of the positioning member 140, as shown in FIG. 2B.

Optionally, the positioning member 140 and/or pusher member 130 may include one or more elements that engage when the cartridge 120 reaches a predetermined location when advanced distally along the positioning member 140, e.g., to limit subsequent proximal movement of the pusher member 130 relative to the positioning member 140. For example, as shown in FIGS. 2A and 2B, the positioning member 140 may include a locking element, e.g., a stepped-down region or recess 145 at a predetermined location and the pusher member 130 may include a living hinge, tab, or other latch element 137 on the proximal end 132. Alternatively, the locking element 145 may be a ring, tab, or other raised element (not shown) over which the latch element 137 may pass distally, yet may subsequently engage the latch element 137 to prevent proximal movement of the pusher member 130, as shown in FIG. 3B(3) and described further below. For example, the latch element 137 may simply be an annular notch in the proximal end 132 of the pusher member 130 to bias the proximal end inwardly.

As an alternative to the latch element(s) 137, the pusher member 130 may simply include a relatively narrow region on the proximal end 132. Further alternatively, the latch element(s) 137 may be replaced by a separate collar or sleeve, one or more inwardly oriented detents, and the like (not shown) attached to or otherwise formed on the proximal end 132 of the pusher member 130. In an exemplary embodiment, the locking element 145 may be defined by a reduced diameter region on the positioning member 140, e.g., formed by providing a larger tube around a smaller inner tube or by machining, etching, or otherwise removing a portion of the tubular body of the positioning member 140 distal to the reduced region. The pusher member 130 may include a corresponding element (also not shown) that may allow distal advancement but prevent proximal refraction once the pusher member 130 is advanced a predetermined distance, i.e., over the locking element 145. Exemplary embodiments of cooperating elements are disclosed in U.S. Publications No. 2006/0099238 and 2009/0088793, incorporated by reference herein.

The reduced region or other locking element 145 may be provided at a predetermined location on the positioning member 140, e.g., a predetermined distance from the positioning element 146 that corresponds to a length of the pusher member 130, e.g., a relaxed or compressed length of the pusher member 130. As the cartridge 120 (and consequently the pusher member 130) is advanced over the positioning member 140, e.g., until the sealant 2 is disposed adjacent the positioning element 146, the latch element 137 may pass freely over the locking element 145. Thereafter, the latch element 137 may prevent the pusher member 130 from being retracted again past the locking element 145 due to the blunt edge of the latch element 137 abutting the locking element 145.

Alternatively, the pusher member 130 may be fixed relative to the positioning member 140, for example, mechanically bonded, chemically bonded, interference fit, and the like. For example, the distal end 134 of the pusher member 130 may be fixed a predetermined distance proximal to the positioning element 146, e.g., to provide the sealant 2 immediately adjacent the positioning element 146, as shown in FIG. 2B. Additional information on such alternatives and methods for making and using them may be found in U.S. Publication No. 2008/0082122, incorporated by reference herein.

In one embodiment, the hub 123 of the cartridge 120 includes a tamping or auto advance device 200, depicted in detail in FIGS. 3A and 3B. Generally, the auto advance device 200 includes a slider tube 204 slidable within the housing 202 and coupled to the cartridge 120. The slider tube 204 may be biased distally relative to the housing 202 such that movement of the cartridge 120, sealant 2 (not shown, see FIG. 1A), and pusher tube 130 is initially coupled to the housing 202. Thus, when the hub 123 is directed distally, the cartridge 120, sealant 2, and pusher tube 130 are also directed distally. However, the slider tube 204 may be movable proximally within the housing 202, e.g., when the bias is overcome, to allow the cartridge 120 to move proximally relative to the sealant 2 and pusher member 130, e.g., during deployment of the sealant 2, as described further below.

As best seen in FIG. 3A(3), the proximal end 132 of the pusher member 130 may be disposed within the housing 202 before the apparatus 101 is used. As shown in FIGS. 3A(1)-3A(3), the auto advance device 200 may include an auto advance spring 206 adjacent the slider tube 204, e.g., for biasing the slider tube 204 distally, yet allowing the slider tube 204 to move proximally within the housing 202 when the spring bias is overcome. It will be appreciated that other springs or biasing mechanisms may be provided for biasing the slider tube 204 distally within the housing 202, yet allowing proximal movement relative to the housing 202. In addition, as best seen in FIGS. 3A(1) and 3A(2), the auto advance device 200 may include auto advance spring support tubing 208 fixed relative to the housing 202 and around which the auto advance spring 206 may be disposed. The slider tube 204 may slide over the support tubing 208 when the slider tube 204 is directed proximally within the housing 202.

In addition, the auto advance device 200 may include one or more additional components, e.g., coupled to the pusher member 130, cartridge 120, and/or housing 202. For example, the pusher tube spring 210 may be disposed between the secondary pusher member 230 and the proximal end 132 of the pusher member 130. The pusher tube spring 210 may be coupled to the pusher member 130 and the secondary pusher member 230, e.g., by one or more of an interference fit, bonding with adhesive, and the like. In this embodiment, the proximal end 132 of the pusher member 130 is positioned in the distal end 210a of the tamping spring 210 and the distal end of the secondary pusher member 230 is positioned within the proximal end 210b of the tamping spring 210. Thus, the outside diameters of the pusher members 130 and 230 are slightly less than the inside diameter of the tamping spring 210.

Optionally, the auto advance device 200 may include an inner cartridge or tamping tube 212 disposed around the pusher tube spring 210 and the secondary positioning member 230. As best seen in FIGS. 3A(1) and 3A(2), the inner cartridge 212 may be disposed concentrically within the slider tube 204. The inner cartridge 212 may be coupled to the slider tube 204 such that the inner cartridge 212 moves with the slider tube 204. For example, the inner cartridge 212 may include a hub 212a, which may be received in a corresponding pocket or recess 204a in the slider tube 204, thereby coupling movement of the inner cartridge 212 to the slider tube 204. The inner cartridge 212 may also protect and/or conceal the pusher tube spring 210 therein and may be coupled to the proximal end 122 of the cartridge 120. As best seen in FIG. 3A(2), the inner cartridge 212 may have an outer diameter similar to the diameter of the cartridge 120, e.g., such that the inner cartridge 212 abuts the proximal end 122 of the cartridge 120. Alternatively, the inner cartridge 212 may be attached to the proximal end 122 of the cartridge 120. In a further alternative, the inner cartridge 212 and cartridge 120 may be provided as a single piece, e.g., such that the inner cartridge 212 is merely an extension (not shown) extending proximally from the cartridge 120.

In FIGS. 3A(1)-3A(3), the auto advance device 200 is in an "inactive" position where the springs 206 and 210 are in extended or relatively relaxed states (best seen in FIG. 3A(2)). In the inactive position, the slider tube 204 may be biased by the auto advance spring 206 such that a flange 218 extending from the slider tube 204 abuts or otherwise contacts a distal rib 214 of the housing 202, as best seen in FIG. 3A(1). Thus, the slider tube 204 may be positioned in a distal portion of the housing 202 in the inactive position. In addition, in the inactive position, the support tubing 208 may be positioned proximally to and/or substantially entirely outside of the slider tube 204, also as best seen in FIG. 3A(1). As shown in FIG. 3A(3), the secondary pusher member 230 is located proximal to the locking element 145 in the inactive position, e.g., such that movement of the pusher member 130 and secondary pusher member 230 are initially coupled to movement of the cartridge 120.

FIGS. 3B(1)-3B(3) show the auto advance device 200 in an "active" position where the springs 210 and 206 are compressed or in a relatively higher potential energy state. In the active position, the housing 202, including the cartridge 120, sealant 2, pusher member 130, and slider tube 204 have been advanced distally relative to the positioning member 140 such that the secondary pusher member 202 has been advanced distally past the locking element 145, as best seen in FIG. 3B(3). In the active position, the auto advance spring 206 is compressed between a proximal rib 216 of the housing 202 and the proximal end of the slider tube 204, and the slider tube 204 is positioned in a proximal portion of the housing 202. For example, the cartridge 120 and hub 123 may be advanced relative to the positioning member 140 until the cartridge 120 cannot be advanced further, whereupon additional distal movement of the hub 123 causes the auto advance spring 206 to compress as the slider tube 204 (and proximal end 122 of the cartridge 120) moves proximally within the housing 202. In addition, in the active position, the support tubing 208 may extend into the slider tube 204 and abut the secondary pusher member 230, thus compressing the tamping spring 210 as the pusher member 130 moves proximally with the cartridge 120, as best seen by comparing FIG. 3B(2) with FIG. 3A(2). When compressed, the tamping spring 210 applies a distal force against the pusher member 130, biasing the pusher member 130 distally against the sealant 2. As explained further below, as the sealant 2 expands and/or softens, e.g., upon exposure to an aqueous environment, the constant force applied by the tamping spring 210 causes the pusher member 130 to automatically advance distally, exerting constant force on the sealant 2, thereby tamping or "cinching" the sealant 2 between the pusher member 130 and the positioning element 146 during expansion. This method is described in greater detail below.

In the embodiment shown, the springs 210 and 206 are compression springs that are in an expanded condition at their relatively relaxed length and/or lower potential energy state and are in a compressed condition and/or higher potential energy state when a load is applied. Alternatively, instead of the compression springs 210 and 206, the auto advance device 200 may include other spring arrangements or biasing mechanisms, such as an extension spring, leaf spring, and the like (not shown), e.g., that may be in a compressed condition at its lower energy state length and in an expanded condition when a load is applied.

Turning to FIGS. 4A-8B, an exemplary method is shown for sealing a puncture 90, e.g., using the system 10 described above to deliver a sealant 2, e.g., to achieve hemostasis within the puncture 90. Generally, the puncture 90 extends from a patient's skin 92 through intervening tissue 96, e.g., to a body lumen 94. In an exemplary embodiment, the puncture 90 may be a percutaneous puncture communicating with a blood vessel 94, such as a femoral artery, carotid artery, and the like.

Figure 4A:
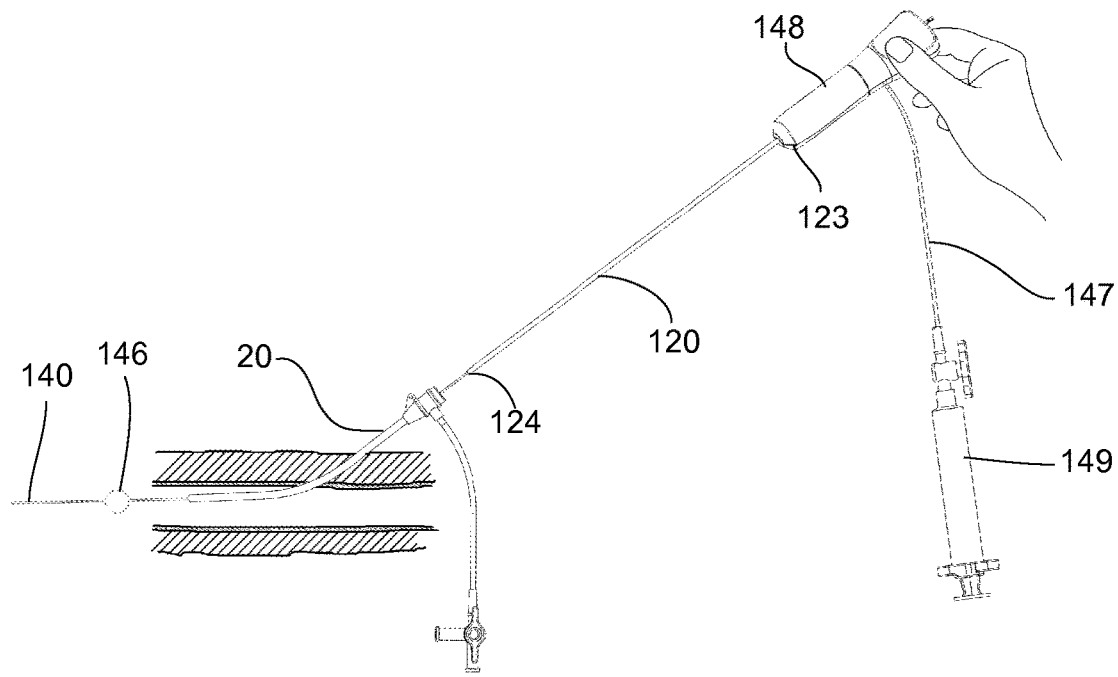
FIGS. 4A, 5A, 6A, 7A, and 8A are partial cross-sectional views of a patient's body illustrating a method of using the system of FIG. 1A for sealing a puncture through tissue.
Figure 4B:
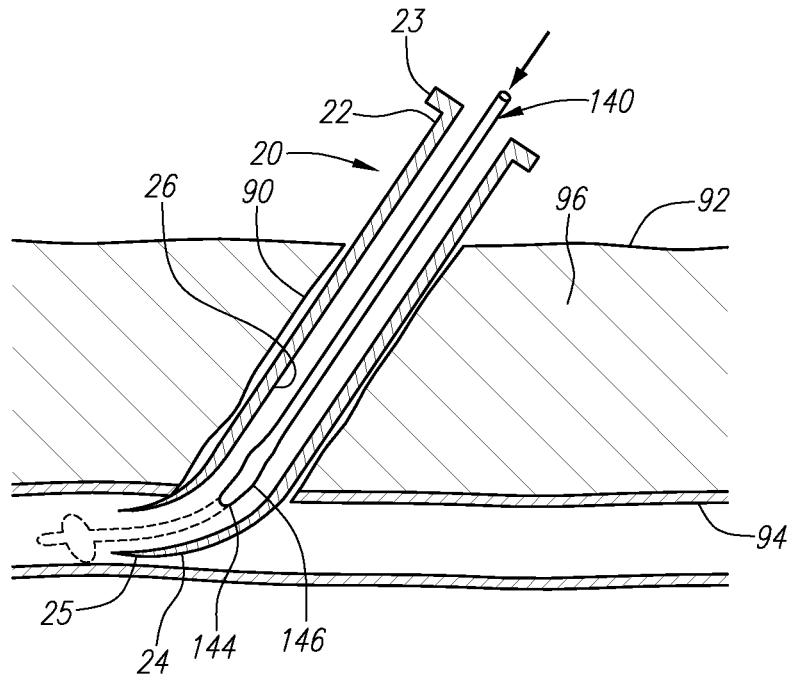
FIGS. 4B, 5B, 6B, 7B, and 8B are cross-sectional detail views of the method of FIGS. 4A, 5A, 6A, 7A, and 8A.

In an exemplary method, the puncture 90 may be created using known procedures, e.g., using a needle, guidewire, one or more dilators, and the like (not shown). Then, as depicted in FIGS. 4A and 4B, an introducer sheath 20 may be advanced through the puncture 90 into the vessel 94, e.g., over a guide wire (not shown) placed through the puncture 90 into the vessel 94. The introducer sheath 20 may provide access into the vessel 94 for one or more instruments, e.g., to allow one or more diagnostic, therapeutic, and/or other interventional procedures to be performed via the vessel 94. Upon completing the procedure(s) via the vessel 94, any such instrument(s) may be removed from the puncture 90, leaving the introducer sheath 20 extending through the puncture 90 into the vessel 94.

The distal end 144 of the positioning member 140 may be introduced into the puncture 90, e.g., through the lumen 26 of the introducer sheath 20, with the positioning element 146 in a collapsed condition, as shown in FIG. 4B. As shown in FIG. 4A, the cartridge 120 and cartridge hub 123, along with the sealant 2 and pusher member 130 (not shown in FIG. 4A for clarity, see, e.g., FIGS. 1A-2B), may be provided initially on the proximal end of the positioning member 140, e.g. near the positioning member housing 148. Thus, the distal end 124 of the cartridge 120 may initially be located outside the puncture 90 when the positioning member 140 is advanced into the puncture 90. Alternatively, the cartridge 120 may be carried on the distal end 144 of the positioning member 140, e.g., as shown in FIG. 2B, such that the cartridge 120 (along with the sealant 2 and pusher member 130) is introduced simultaneously with the positioning member 140, as described in U.S. Publication No. 2008/0082122, incorporated by reference herein.

Still referring to FIGS. 4A and 4B, the distal end 144 of the positioning member 140 may be inserted through the puncture 90 (via the introducer sheath 20) and into the vessel 94. Optionally, the positioning member 140 may include one or more markers (not shown) that may be disposed adjacent the proximal end 22 of the introducer sheath 20 when the distal end 144 extends beyond the distal end 24 of the introducer sheath 20, e.g., to provide a visual indication that the positioning element 146 is disposed within the vessel 94 beyond the distal end 24 of the introducer sheath 20. Once the positioning element 146 is disposed within the vessel 94, i.e., beyond the distal end 24 of the introducer sheath 20, the positioning element 146 may be expanded to an enlarged condition, as shown in FIG. 4A and as shown in phantom in FIG. 4B. After expanding the positioning element 146, the positioning member 140 may be at least partially withdrawn until the positioning element 146 contacts the wall of the vessel 94 (shown in FIGS. 5A and 5B), e.g., to substantially seal the vessel 94 from the puncture 90.

Figure 5A:
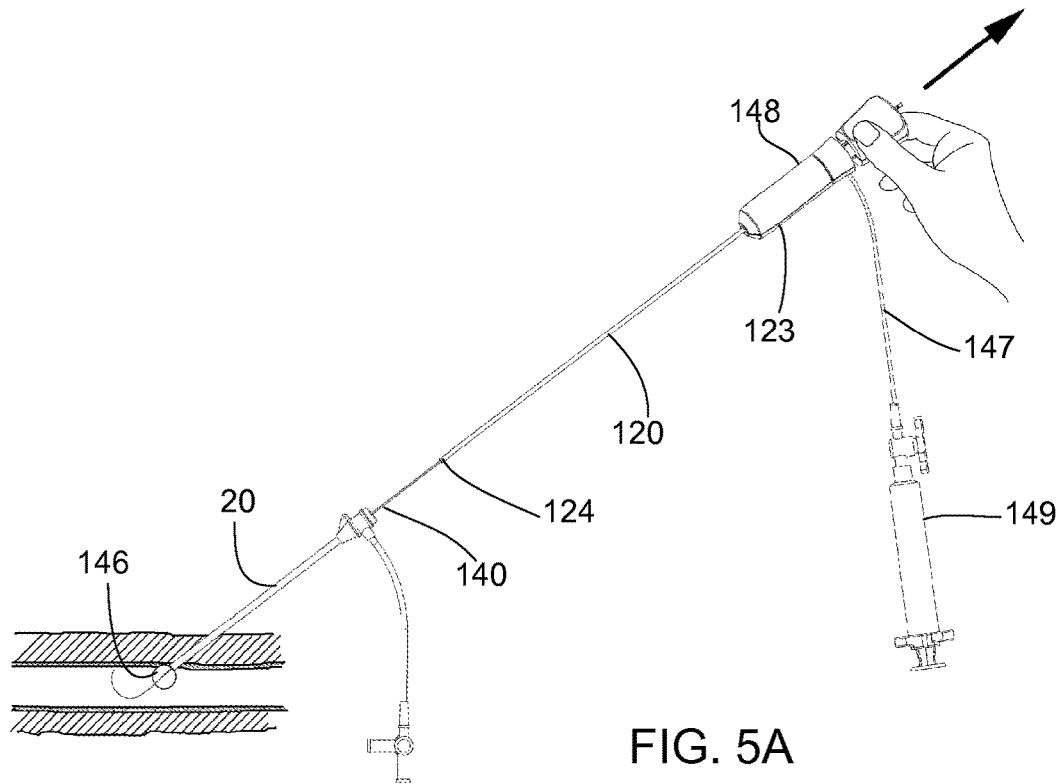
Figure 5B:
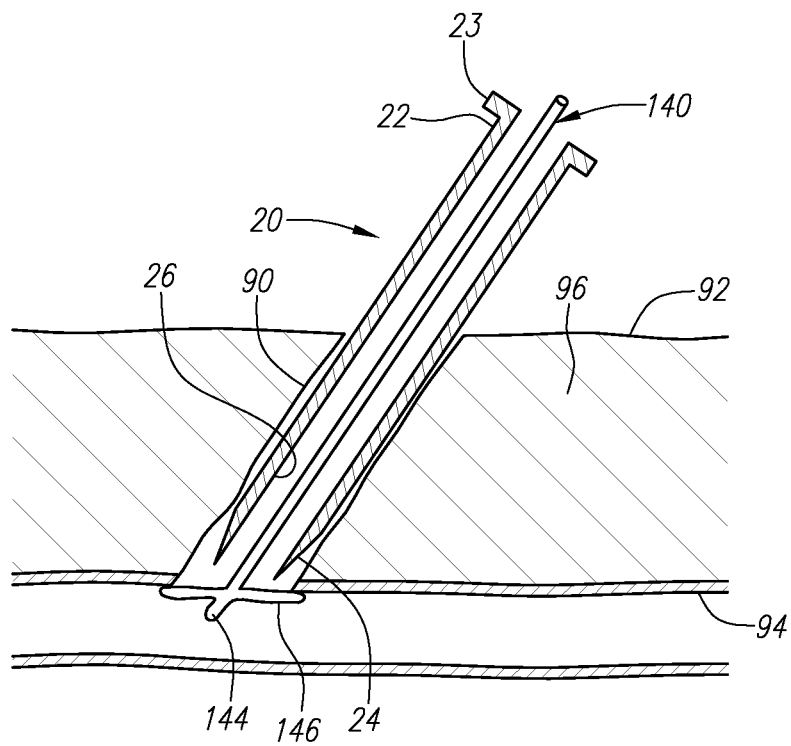

In an exemplary method, this may involve a two-step process (although it may be completed in a single continuous action). First, with the positioning element 146 expanded within the vessel 94, as shown in FIG. 4A and in phantom in FIG. 4B, the positioning member 140 may be withdrawn until the positioning element 146 contacts the distal end 24 of the introducer sheath 20, which may provide a first tactile feedback to the user (i.e., that the positioning element 146 has contacted the introducer sheath 20, e.g., based upon the increased weight and/or resistance to proximal movement). After encountering the first tactile feedback, the positioning member 140 may be withdrawn further until the positioning element 146 contacts the wall of the vessel 94 and resists further withdrawal, thereby providing a second tactile feedback. The introducer sheath 20 may be pulled proximally by the positioning element 146 as the positioning member 140 is withdrawn, e.g., until the positioning element 146 contacts the wall of the vessel 94 and the distal end 24 of the introducer sheath 20 is withdrawn from the vessel 94 into the puncture 90, as shown in FIGS. 5A and 5B.

Alternatively, a tension indicator assembly (not shown) may be used for more accurate control of the proximal tension on the positioning member 140. Exemplary tension indicator assemblies are disclosed in co-pending U.S. patent application Ser. No. 12/098,380, filed Apr. 4, 2008, and published as U.S. Publication No. 2009/0254110, the entire disclosure of which is expressly incorporated herein by reference.

The desired amount of proximal tension may be maintained manually or using a tension device (not shown) to provide temporary hemostasis, e.g., during the subsequent steps. Exemplary tension devices are disclosed in co-pending U.S. patent application Ser. No. 10/806,952, filed Mar. 22, 2004 and published as US 2004/0267308, the entire disclosure of which is expressly incorporated herein by reference.

Figure 6A:
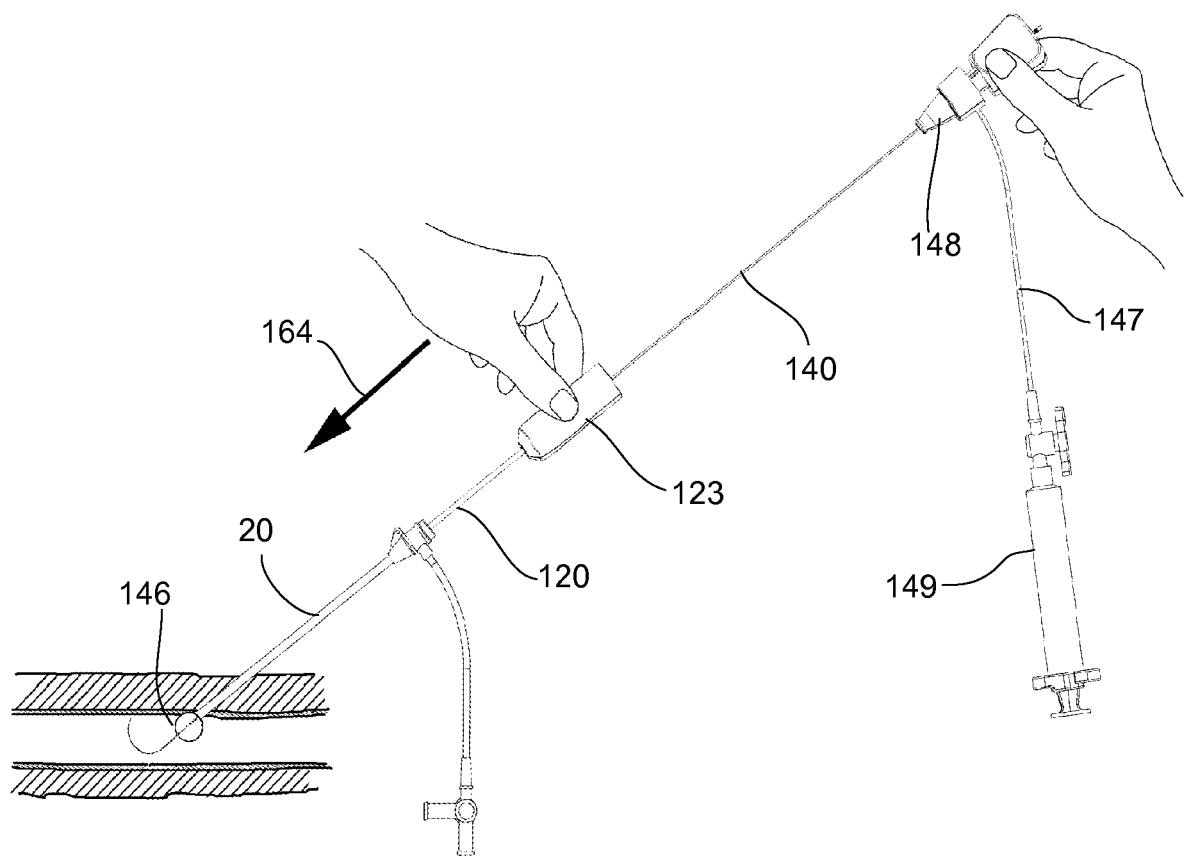
Figure 6B:
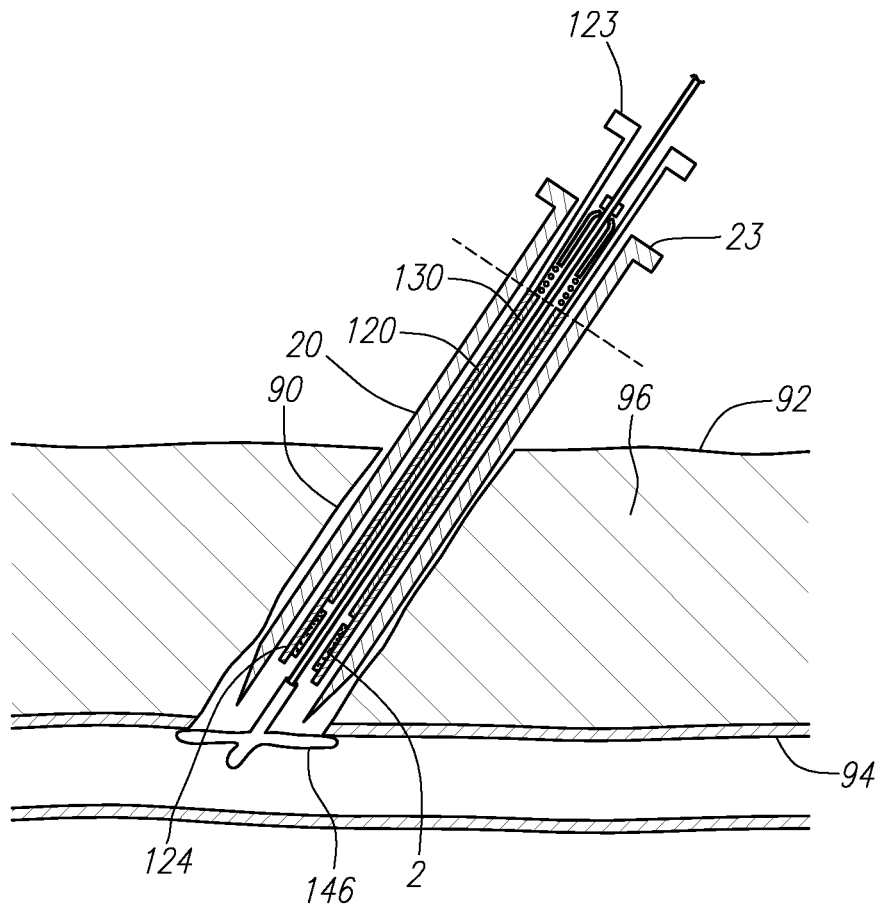

Turning to FIGS. 6A and 6B, the cartridge 120 (carrying the sealant 2, shown in FIG. 6B) may then be advanced distally over the positioning member 140 into the puncture 90, as indicated by arrow 164. For example, FIG. 6A illustrates the user grasping the hub 123 and pushing the hub 123, e.g., to separate the hub 123 from the positioning member housing 148 and advance the cartridge 120 distally over the positioning member 140 and into the introducer sheath 20. The cartridge 120 may be advanced into the introducer sheath 20 until the distal end 124 of the cartridge 120 contacts the expanded positioning element 146, as shown in FIG. 6B.

In one embodiment, the cartridge 120 may be advanced through the introducer sheath 20 until a hub 123 of the cartridge 120 abuts a hub 23 on the introducer sheath 20. In another embodiment, the cartridge 120 may be advanced until a locking element (not shown) engages, thereby coupling the cartridge 120 to the introducer sheath 20.

In the embodiment where the cartridge hub 123 includes the auto advance device 200, the auto advance device 200 is initially in the inactive position (not shown, see, e.g., FIGS. 3A(1)-3A(3)), during distal advancement of the hub 123 and the cartridge 120. Thus, distal advancement of the hub 123 causes corresponding advancement of the cartridge 120. Once the cartridge 120 contacts the expanded positioning element 146, further distal advancement of the cartridge 120 is prevented by the positioning element 146.

Figure 6C:
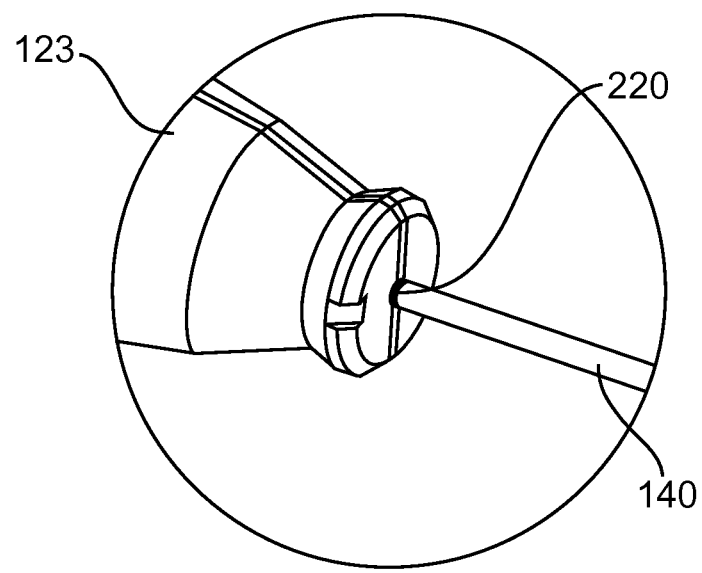
FIGS. 6C and 6D are perspective views of a proximal end of a hub on the cartridge of the system of FIG. 1A before and after the hub passes a marker on the positioning member, respectively.

Then, when the hub 123 is advanced further distally relative to the cartridge 120 the auto advance device 200 may be activated. For example, as shown in FIG. 6C, the cartridge 120 and hub 123 may be advanced until a marker 220 on the positioning member 140 becomes initially exposed, which may indicate that the distal end 124 of the cartridge 120 is adjacent to or in contact with the expanded positioning element 146. At this stage, as shown in FIGS. 3A(1)-3A(3), the slider tube 204 may be in the distal position within the housing 202 of the hub 123. The hub 123 may then be advanced further, e.g., at least partially over the cartridge 120, as shown in FIGS. 3B(1)-3B(3).

Figure 6D:
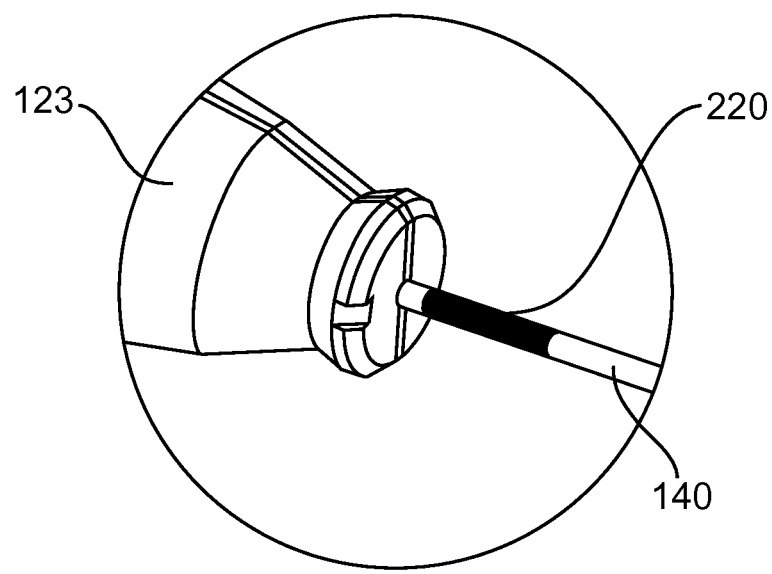

As shown in FIG. 6D, as the hub 123 is advanced, the marker 220 on the positioning member 140 may become entirely exposed, thereby providing a visual indicator to the user confirming that the auto advance device 200 has been activated. It will be appreciated that other visual and/or audible indicators (not shown) may be provided on the positioning member 140 and/or hub 123 to provide confirmation when the secondary pusher member 230 has been sufficiently advanced and/or the tamping spring 210 has been compressed. Since the cartridge 120 is prevented from moving distally, distal advancement of the hub 123 causes the slider tube 204, which is fixed to the cartridge 120, to slide into a proximal portion of the hub 123 so that the proximal end of the slider tube 204 contacts the proximal end of the hub 123, as shown in FIGS. 3B(1)-3B(3). Distal advancement of the hub 123 further causes the auto advance spring 206 to compress between the proximal end of the slider tube 204 and the proximal rib 216 of the housing 202. In the active position, the auto advance spring support tubing 208 extends into the tamping tube 212, thereby pushing the secondary pusher member 230 towards the proximal end 132 of the pusher member 130, which causes the tamping spring 210 to compress. As the secondary pusher member 230 moves towards the proximal end 132 of the pusher member 130, the latch element 237 passes over the raised element 145 on the positioning member 140. Thereafter, the secondary pusher member 230 is prevented from retracting proximally relative to the positioning member 140 and the compression of the tamping spring 210 is maintained, thus providing constant force to the sealant 2 via the pusher member 130.

Figure 7A:
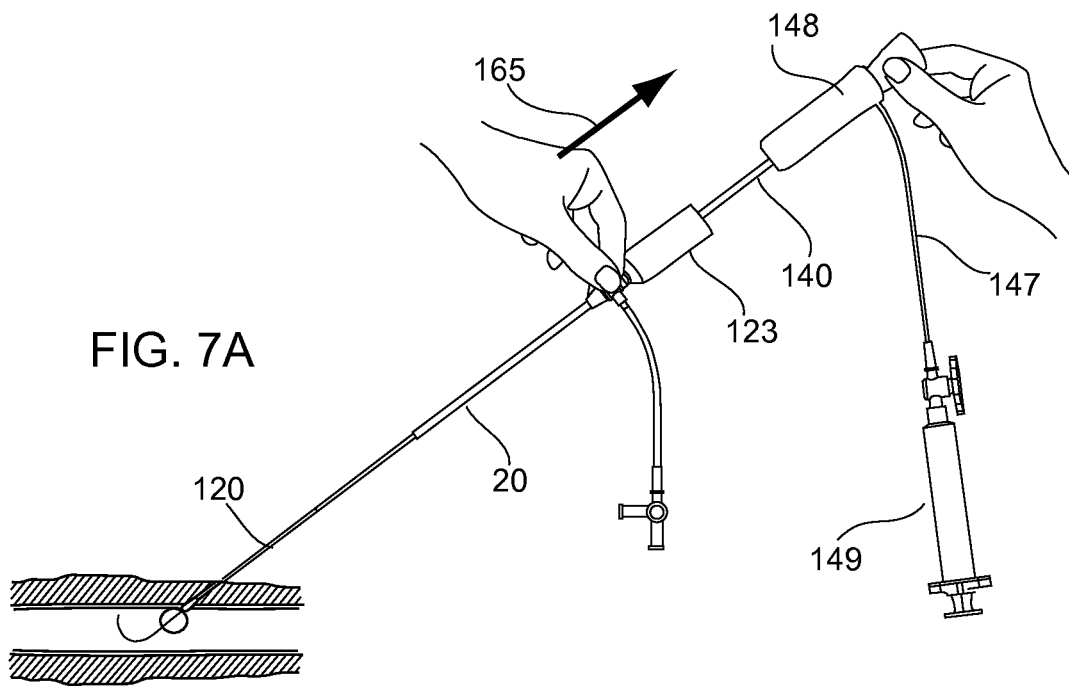
Figure 7B:
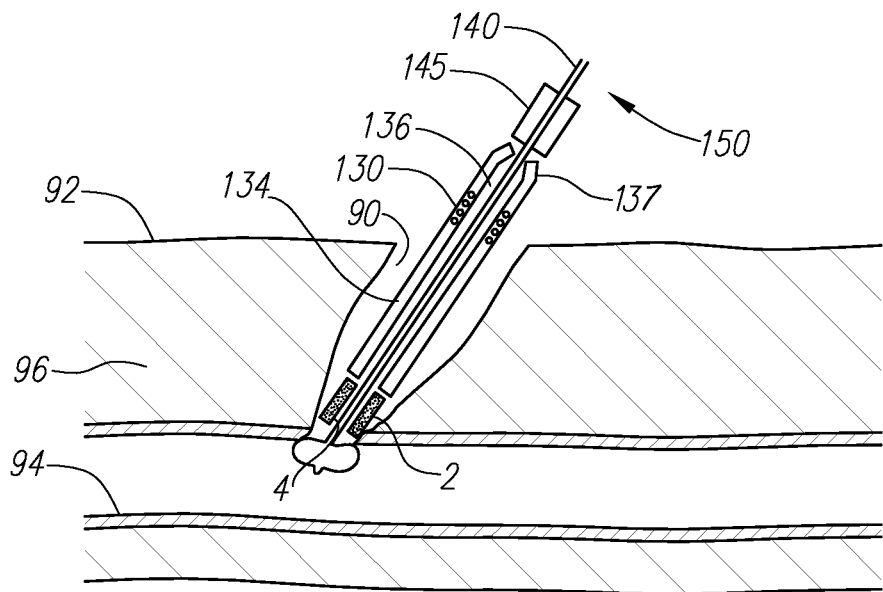

Returning to FIGS. 6A and 6B, once the cartridge 120 and hub 123 have been advanced to place the sealant 2 in the desired position within the puncture 90 (best seen in FIG. 6B), the cartridge 120 may be retracted, e.g., by pulling proximally on the hub 123, as indicated by arrow 165 in FIG. 7A. If the optional locking element (not shown) has coupled the introducer sheath 20 to the cartridge 120, this action also withdraws the introducer sheath 20 from the puncture 90. Alternatively, the introducer sheath 20 may be pulled, contacting the hub 123 and thereby withdrawing the cartridge 120 along with the introducer sheath 20. As the cartridge 120 is retracted, the pusher member 130 may remain in place (e.g., due to the locking element 145) to prevent substantial proximal movement of the sealant 2, the sealant 2 is exposed within the puncture 90, as shown in FIG. 7B. In one embodiment, as described above, when the cartridge 120 is retracted, the latch element 237 on the secondary pusher member 230 may abut the locking element 145, thereby preventing substantial proximal retraction of the secondary pusher member 230 and the sealant 2 adjacent to the distal end 134 of the pusher member 130.

When the sealant 2 is exposed within the puncture 90, the sealant 2 may be exposed to blood and/or other body fluids within the puncture 90. This exposure may cause the sealant 2 to absorb fluid, soften and/or expand within the puncture 90, e.g., to provide hemostasis. The auto advance device 200 may cause the pusher tube 130 to automatically advance as space permits, e.g., when the sealant 2 begins to swell and/or soften, thereby compressing or "cinching" the sealant 2 between the pusher tube 130 and the positioning element 146. Optionally, if desired, the pusher member 130 may be advanced manually to compress the sealant 2 further, e.g., against the positioning element 146. This may cause the sealant 2 to expand further radially outwardly and/or press the sealant 2 against the arteriotomy, e.g., to enhance sealing the puncture 90 from the vessel 94. Optionally, the pusher member 130 may include one or more distance markers (not shown) on or adjacent the proximal end 132, and the pusher member 130 may be advanced into the puncture 90 a desired distance, which may be confirmed by monitoring the distance markers.

Figure 8A:
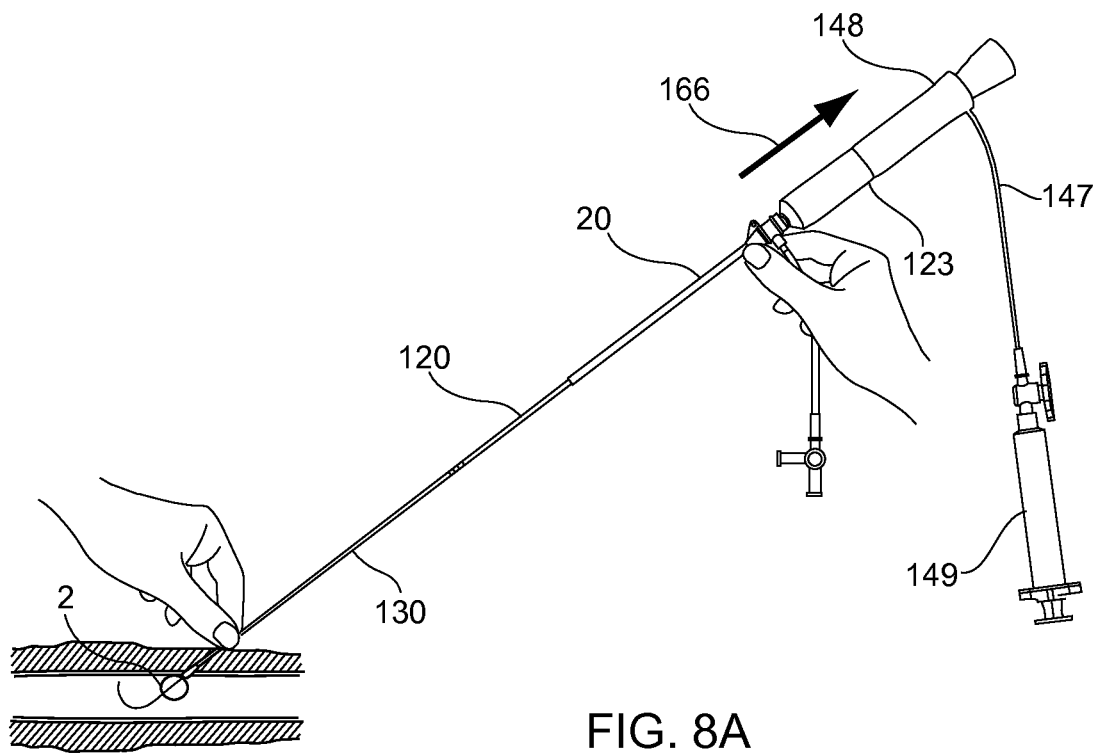
Figure 8B:
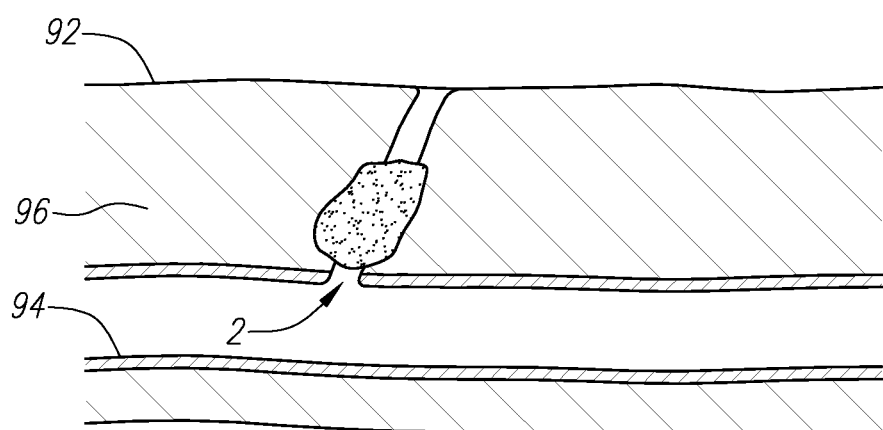

Once the sealant 2 has been exposed for sufficient time and/or tamped by the pusher member 130, the positioning element 146 may be collapsed, and the positioning member 140 withdrawn from the vessel 94 and puncture 90, e.g., by pulling the collapsed positioning element 146 through the sealant 2 and pusher member 130, as depicted by arrow 166 in FIG. 8A. In an exemplary embodiment, the expandable member 146 may have a profile not more than about 0.875 millimeter (035 inch) to facilitate removal of the positioning member 140 without substantially disturbing the deployed sealant 2. The pusher member 130 may be maintained substantially stationary during withdrawal of the positioning member 140, e.g., to prevent migration and/or dislodgment of the sealant 2 within the puncture 90. For example, as shown in FIG. 8A, the pusher member 130 may be maintained substantially stationary by a user grasping the pusher member 130 during withdrawal of the positioning member 140. In the embodiment where the system 10 includes the auto advance device 200, the user may grasp the pusher member 130 rather than the secondary pusher member 230 so that the user may have more control of the force applied to the sealant 2 during withdrawal of the positioning member 140. In addition, in embodiments where the sealant 2 includes an adherent layer, the "sticky" adherent layer may also aid in securing the sealant 2 to the surrounding tissue. Once the positioning member 140 is completely removed, the pusher member 130 may be removed from the puncture 90, leaving the sealant 2 within the puncture 90, as shown in FIG. 8B.

Optionally, after removing the positioning member 140, liquid hydrogel or other sealing compound, or other material may be delivered into the puncture 90, e.g., above and/or around the sealant 2, to assist in achieving hemostasis. For example, such material may be delivered via the lumen 136 of the pusher member 130 and/or by introducing another delivery device (not shown) into the puncture 90, e.g., after removing the pusher member 130.

Turning now to FIGS. 9-11B, another exemplary embodiment of an apparatus 301 is shown for delivering a sealant 302 into a puncture through tissue including a tamping device 385. Similar to other embodiments herein, the apparatus 301 is shown schematically and not to scale, e.g., with the radial and axial dimensions exaggerated to facilitate identification of the components of the apparatus 301. The apparatus 301 includes an elongate positioning or occlusion member 340, a cartridge 370, and a catheter hub 380. The positioning member 340 includes a proximal end 342, a distal end 344, and an expandable positioning element 346, e.g., similar to previous embodiments, on the distal end 344. Similar to previous embodiments, optionally, a transition cuff 350 may be located adjacent to the distal end of the expandable member 346.

The cartridge 370 generally includes an outer tubular member 373, a sealant 302, an inner pusher member 330, and a middle hub 376. The outer tubular member 373 includes a lumen 360 extending between a proximal end 372 and a distal end 374 thereof. The outer tubular member 373 is movable relative to the inner pusher member 330, which is slidably disposed within the outer tubular member 373. The middle hub 376 may be attached to the proximal end 372 of the outer tubular member 373.

Figure 10A:
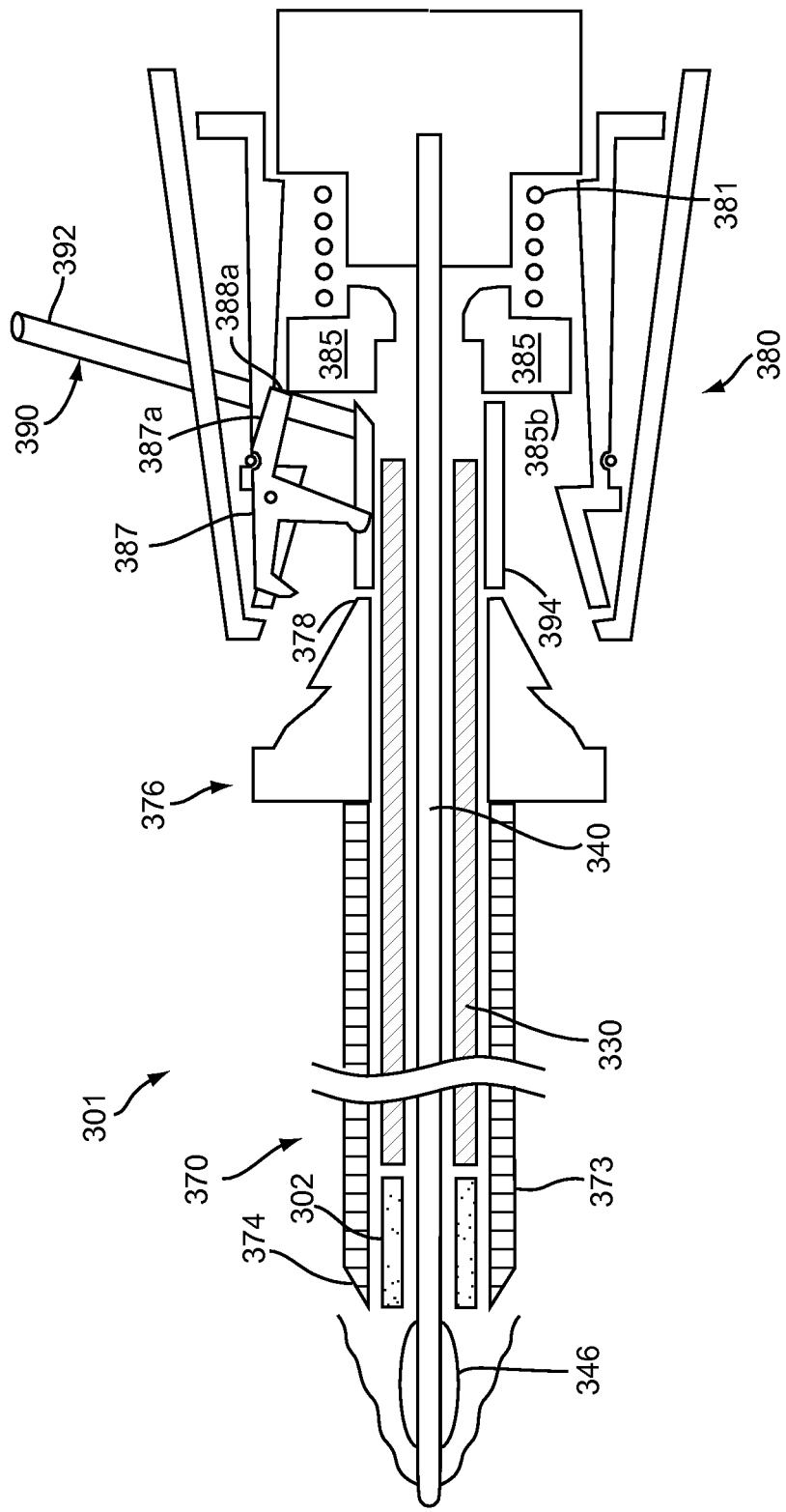
FIGS. 10A-10B are cross-sectional views of the apparatus of FIG. 9 in a first position.
Figure 10B:
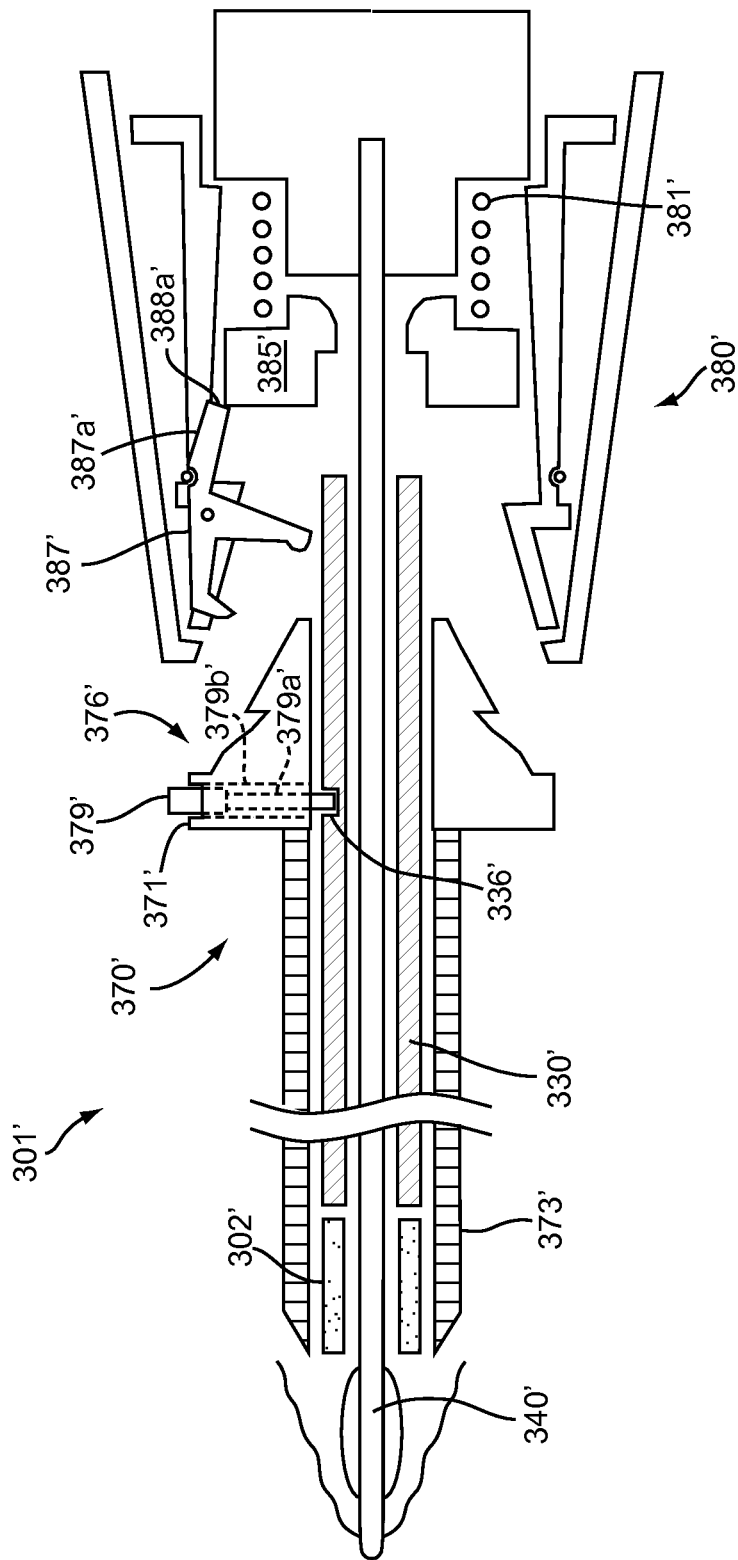

The sealant 302 and inner pusher member 330 are similar to previous embodiments. The inner pusher member 330 includes a lumen extending between a proximal end 332 and a distal end 334. The inner pusher member 330 may include a peel away lock 390 or detents 336, e.g., as shown in FIGS. 10A-10B, for initially limiting proximal movement of the outer tubular member 373, e.g., until after removing the lock 390.

The middle hub 376 includes a main cylinder 371, a first conical surface 377a, and a second conical surface 377b. A latching detent 375 is disposed between the first and second conical surfaces 377a, 377b. The main cylinder 371 includes a proximal ridge 371a, and a distal surface 371b. The first conical surface 377a is tapered from the proximal ridge 371a to the latching detent 375. The distal end of the second conical surface 377b includes a diameter larger than the proximal end of the first conical surface 377a thereby creating the latching detent 375. Alternatively, the first conical surface 377a may be tapered using multiple angles or may be tapered gradually.

The catheter hub 380 includes an outer housing 380a including proximal and distal ends 382, 384 that are substantially fixed relative to the proximal end 342 of the positioning member 340. For example, the catheter hub 380 may include an inner housing 380b fixed relative to the outer housing 380a and coupled to a handle or balloon inflator 396 on the positioning member 340. The hub 380 may also include a tamping device 385, latch 387, and a tamping spring 381 disposed between the tamping device 385 and the balloon inflator 396. The catheter hub 380 may further include centering surfaces 386, e.g., on the inner housing 380b. The material of the catheter hub 380 and other components may be formed from suitable durable plastics, metals, and/or composite materials. During operation of the apparatus 301, the interior of the handle or balloon inflator 396 may communicate via a lumen (not shown) of the positioning member 340 with the interior of the expandable member 346 to provide a fluid to expand the expandable member 346, e.g., similar to other embodiments described elsewhere herein. Optionally, the handle 396 may include a tension indicator (not shown), e.g., also similar to the other embodiments described herein.

The tamping device 385 includes a proximal surface 385a, a distal surface 385b, a proximal nub 385c, and a recess 385d. The recess 385d extends partially through the tamping device 385 between the distal surface 385b and a most distal portion 385e of proximal nub 385c. The recess 385d is sized to receive the proximal end 332 of the inner pusher member 330 therein without allowing the inner pusher member 330 to pass entirely through the tamping device 385.

The latch 387 includes a proximal arm 387a, a distal arm 387b, and an intermediate arm 387c. The proximal, distal, and intermediate arms 387a, 387b, 387c each include a proximal, distal, and intermediate tip 388a, 388b, 388c, respectively. The distal tip 388b may be shaped to mate with the latching detent 375 of the middle hub 376, and the intermediate tip 388c may be shaped with a nub for making initial contact with the proximal end 378 of the middle hub 376. A circular spring clip 383 abuts the proximal arm 387a to bias the proximal arm 387a radially inwardly (away from the inner housing 380b. The inwardly biased proximal arm 387a causes the proximal tip 388a to prevent distal movement of the tamping device 385 when the latch 387 is in the position shown in FIG. 9.

The centering surfaces 386 are located proximally to the distal end 384. The centering surfaces 386 may be conically shaped and/or otherwise sized and/or shaped for cooperating with conical surfaces 377a, 377b on the middle hub 376. The cooperation of centering surfaces 386 with conical surfaces 377a, 377b provides automatic centering during engagement of the middle hub 376 to the catheter hub 380.

Figure 9:
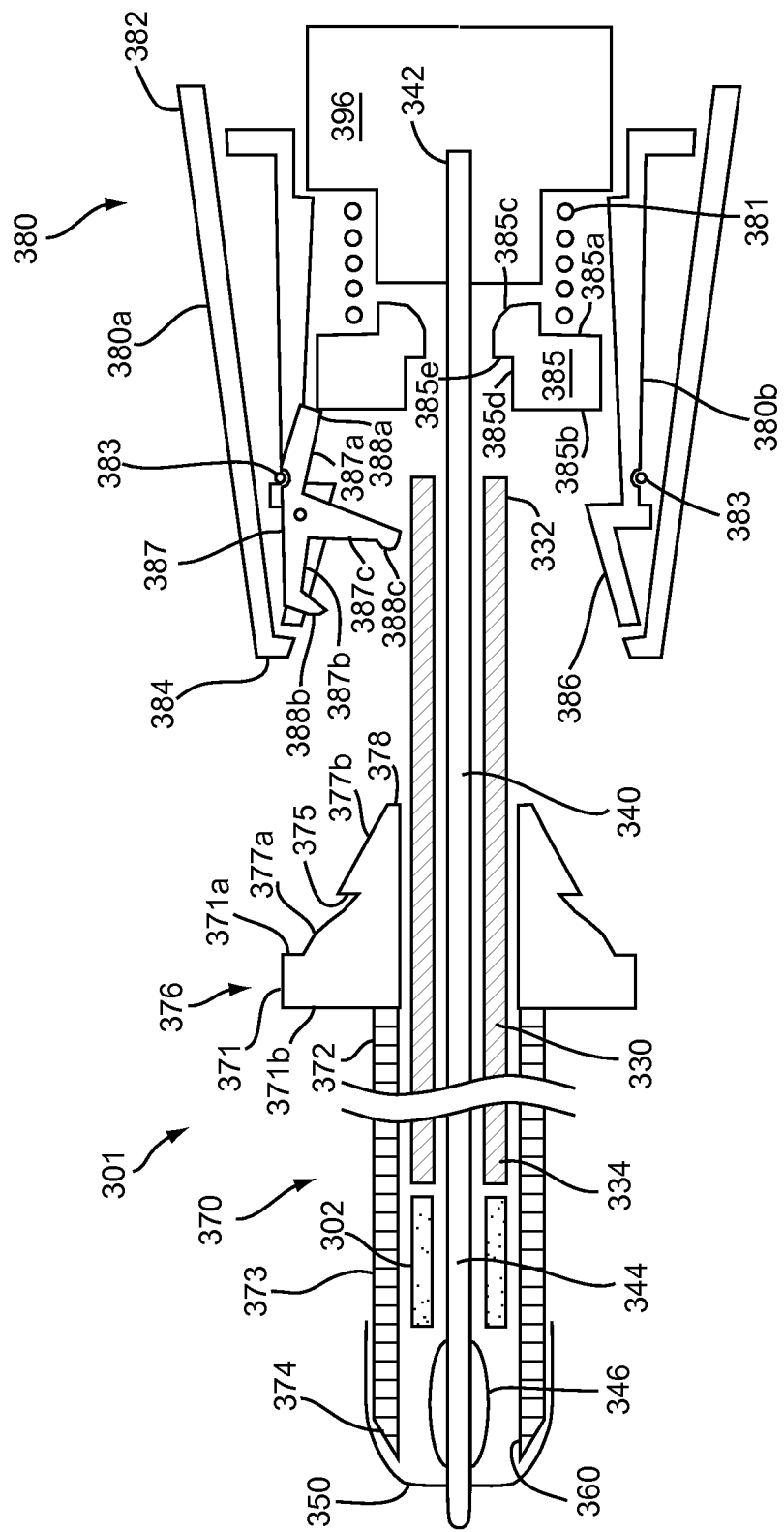
FIG. 9 is a cross-sectional view of another embodiment of an apparatus for delivering sealant into a puncture through tissue, including a tamping device.

FIG. 9 shows the apparatus 301 in a first position, e.g., where the cartridge 370 is disposed adjacent a distal end 344 of the positioning member 340. This first position may be a configuration in which the apparatus 301 is delivered from a manufacturer to a user. In the first position, the transition cuff 350, if included, is fully extended over the distal end 374 of the outer tubular member 373. Further, in the first position, the expandable member 346 may be fully disposed within the lumen 376 of the outer tubular member 373, the tamping device 385 may rest against the proximal tip 388a of the proximal arm 387a, and the tamping spring 381 may be compressed.

Turning to FIG. 10A, the apparatus 301 of FIG. 9 is shown in a second position limited by a peel away lock 390. Alternatively, the apparatus 301 may be provided to the user initially in the second position, i.e., with the cartridge 370 disposed adjacent the catheter hub 380 but without activating the tamping device 385. For example, proximal movement of the cartridge 370 into the catheter hub 380 past the second position may be prevented until the peel away lock 390 is removed. The peel away lock 390 includes a passage extending between a proximal end 392 and a distal end 394 that surrounds the inner pusher member 330. The peel away lock 390 may be disposed between the proximal end 378 of the middle hub 376 and the distal surface 385b of the tamping device 385. In the second position, the cartridge 370 may be positioned proximally relative to the expandable member 346 such that the expandable member 346 is fully exposed distal to the distal end 374. In addition, in the second position, the distal end of the sealant 302 may be disposed adjacent the distal end 374 of the cartridge 370, and the latch 387 may remain in contact with the distal surface 385b of the tamping device 385.

Turning to FIG. 10B, an alternative embodiment of the apparatus 301' is shown that is generally similar to the embodiment of FIGS. 9 and 10A. Similar to FIG. 10A, the apparatus 301' is shown in the second position; however, unlike the apparatus 301 that is only limited from further proximal movement, the apparatus 301' is positively locked in the second position by a locking bar 379a.' The apparatus 301' also includes a modified middle hub 376' and a modified inner pusher member 330.' The modified middle hub 376' includes a pushbutton 379' coupled to the locking bar 379a.' The pushbutton 379' and the locking bar 379a' are disposed within a lumen 379b' extending between an outer and inner surface of the main cylinder 371.' The pushbutton 379' may be spring loaded to bias the locking bar 379a' into a detent 336' on the pusher member 330.' The pushbutton 379,' familiar to those of ordinary skill in the art, may be a single action type or a double action type used to retract the locking bar 379a' from the detent 336.' The spring loaded locking bar 379a' may be extended into the detent 336' when the positioning member 340,' sealant 302,' and inner pusher member 330' are advanced in a distal direction until the locking bar 379a' aligns with the detent 336.' The locking bar 379a' prevents further proximal movement of the cartridge 370' until the pushbutton 379' is pressed to retract the locking bar 379a.' As shown, in the second position, the tamping device 385' remains in contact with the latch 387.'

Figure 11A:
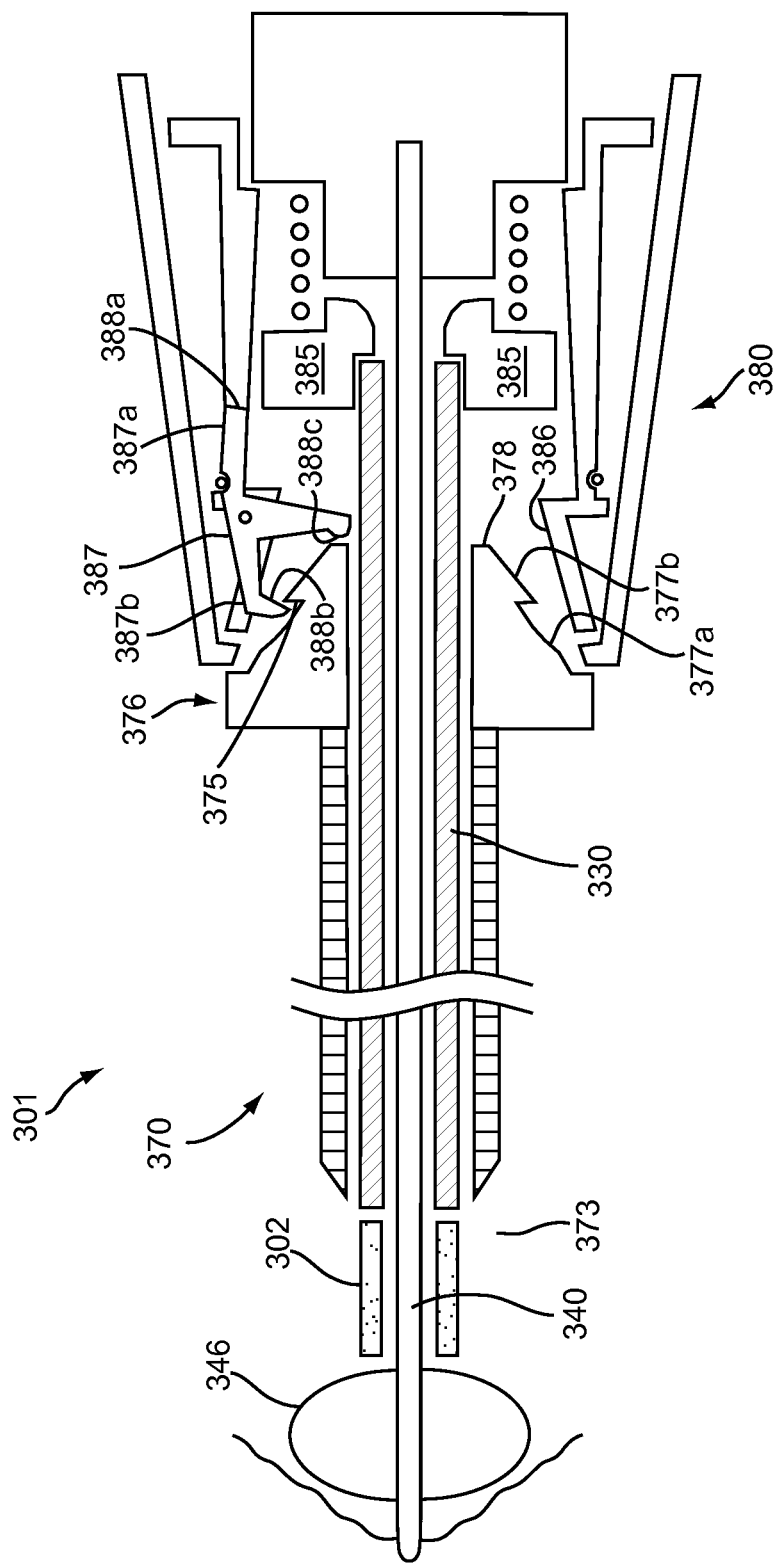
FIGS. 11A-11B are cross-sectional views of the apparatus of FIG. 9 in a second and a third position, respectively.

Turning now to FIG. 11A, after removing the lock 390, the apparatus 301 of FIGS. 9 and 10A is shown in a third position, i.e. at a trigger point, which is a frozen instant in time when the tamping device 385 is initially activated. After releasing the cartridge 370, e.g., by removing the lock 390 or releasing the pushbutton 379,' the cartridge 370 may be moved proximally to expose the sealant 302. As the cartridge 370 enters the catheter hub 380, the conical surfaces 377a, 377b may engage the centering surfaces 386 to align the middle hub 376 with the catheter hub 380. The proximal end 378 of the middle hub 376 first touches the intermediate tip 388c of the intermediate arm 387c, causing the latch 387 to rotate. The latch contact generally occurs before the conical surfaces 377a, 377b and the centering surfaces 386 have fully engaged each other.

Continued proximal movement of the cartridge 370 into the catheter hub 380 to expose the sealant 302 causes the proximal arm 387a and proximal tip 388a to rotate upward away from the tamping device 385, thereby releasing the tamping device 385, as explained further below. Also at the trigger point, the distal arm 387b and distal tip 388b may rotate down into the latching detent 375 to secure the middle hub 376 to the catheter hub 380, thereby securing the cartridge 370 relative to the catheter hub 380 in a latched position.

As shown in FIG. 11A, the expandable member 346 may have been previously expanded and at least partially withdrawn within a body lumen (not shown) as discussed elsewhere herein until the expanded expandable member 346 substantially seals the body lumen from a puncture (also not shown).

Figure 11B:
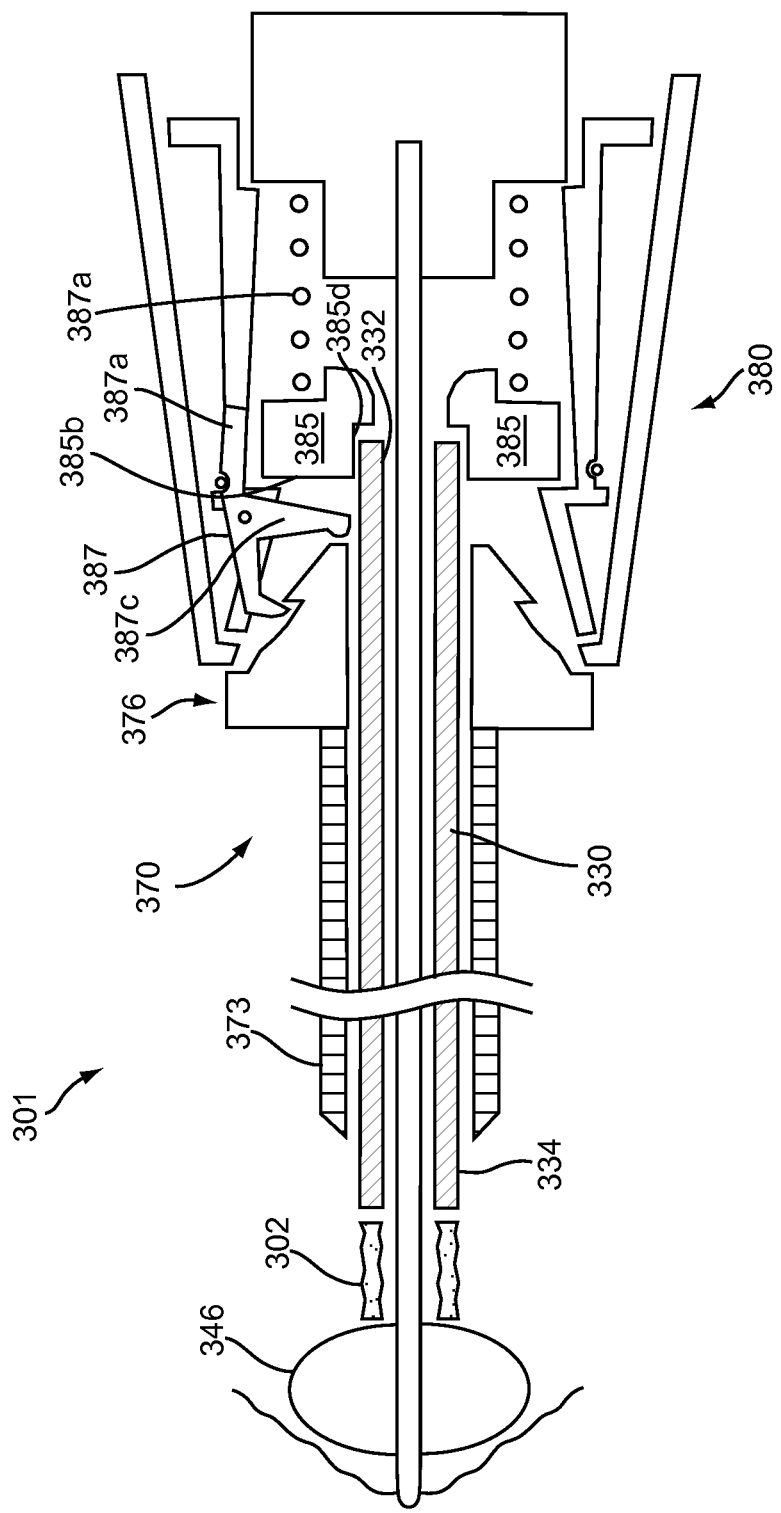

Turning now to FIG. 11B, the apparatus 301 is shown in a third position after the trigger point of FIG. 11A, i.e., with the sealant 302 being tamped and/or compressed. The sealant 302 is tamped between the distal end 334 of the inner pusher member 330, which is biased to move distally, and the expanded expandable member 346. As can be seen, the tamping device 385 is released when the latch 387 is rotated to disengage the proximal arm 387a from the distal surface 385b of the tamping device 385. The tamping spring 381 biases the inner pusher member 330 distally because the proximal end 332 of the inner pusher member 330 is disposed within the recess 385d, thereby biasing the distal end 334 of the inner pusher member 330 distally to compress the sealant 302 towards the expandable member 346 (and/or against an arteriotomy, not shown). The outer surface of the tamping device 385 maintains the proximal arm 387a in an upwardly rotated position, thereby preventing the latch 387 from moving from the latched position.

Thereafter, once the sealant 302 is sufficiently compressed and/or hydrated within the puncture, the catheter hub 380 may be pulled proximally, thereby withdrawing the cartridge 370 from the puncture, leaving the inner pusher member 330 and sealant 302 within the puncture around the positioning member 340, similar to the previous embodiments. The expandable member 346 may then be collapsed and the positioning member 340 removed through the sealant 302 and inner pusher member 330, also similar to the previous embodiments. Finally, the inner pusher member 330 may be removed, leaving the sealant within the puncture.

Figure 12A:
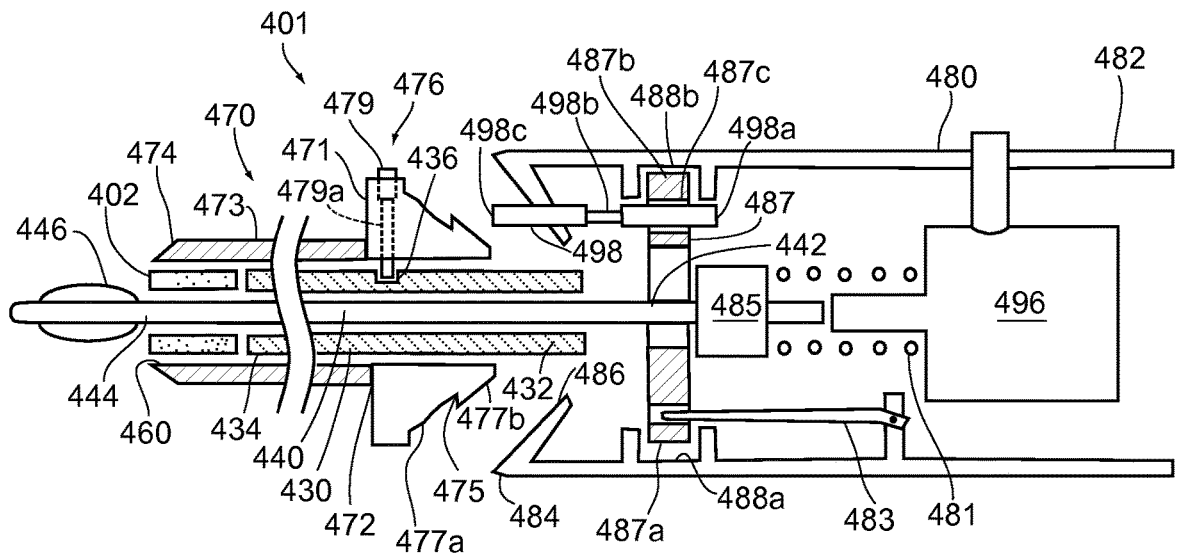
FIGS. 12A-12C are cross-sectional views of another embodiment of an apparatus for delivering sealant into a puncture through tissue, including a tamping device employing a latch gate configuration.
Figure 12B:
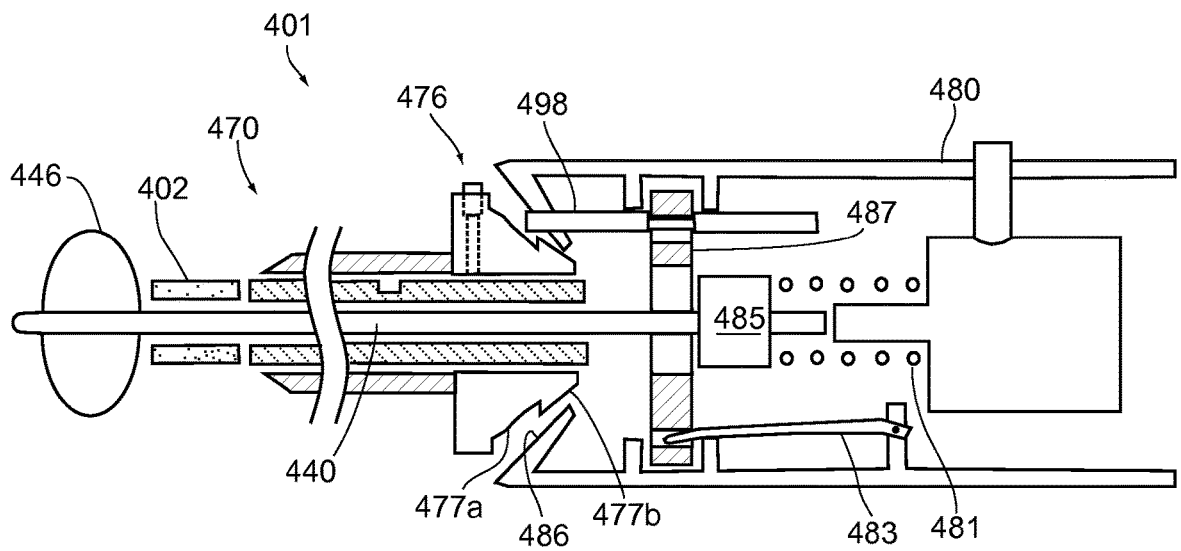
Figure 12C:
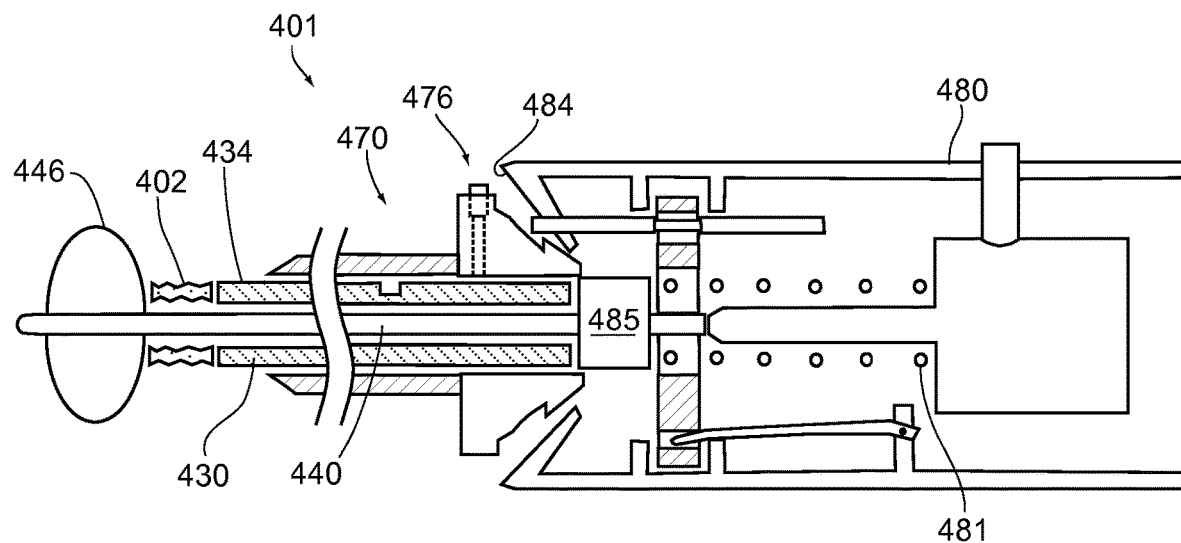

Turning now to FIG. 12A-12C, an alternative embodiment of an apparatus 401 is shown for sealing a puncture. The apparatus 401 generally includes an elongate occlusion or positioning member 440, a cartridge 470, and a catheter hub 480, similar to the previous embodiments. The positioning member 440 is generally similar to those described elsewhere herein and includes a proximal end 442, a distal end 444, and an expandable member 446. Optionally, the apparatus 401 may include a transition cuff (not shown), similar to those described elsewhere herein.

The cartridge 470 includes an outer tubular member 473, a middle hub 476, and a lumen 460 extending between a proximal end 472 and distal end 474 thereof. A sealant 402 and an inner pusher member 430 are disposed within the outer tubular member 473, generally similar to the previous embodiments. The inner pusher member 430 includes a lumen extending between a proximal and distal end 432, 434. The middle hub 476 may be similar to the previous embodiments, e.g., including a main cylinder 471, first conical surface 477a, and second conical surface 477b. A latching detent 475 may be provided, e.g., between the first and second conical surfaces 477a, 477b, also similar to the previous embodiments. The middle hub 476 may also include a pushbutton 479 and/or locking bar 479a for cooperating with a detent 436, similar to the previous embodiments.

The catheter hub 480 generally includes a body or outer housing 480 including proximal and distal ends 482, 484. The body 480 may additionally include a handle or balloon inflator 496, tamping device 485, latch gate 487, and tamping spring 481 disposed between the tamping device 485 and the balloon inflator 496. A trigger pin 498 is coupled between the body 480 and the latch gate 487. The trigger pin 498 includes a proximal end 498a, an intermediate member 498b, and a distal end 498c. The intermediate member 498b is sized smaller than the proximal and distal ends 498a, 498c for releasing the latch gate 487. The body 480 may further include centering surfaces 486. The balloon inflator 496 may be similar to those described elsewhere herein. The latch gate 487 may be initially offset vertically down in the body 480, e.g., with lower and upper ends 487a, 487b disposed in lower and upper guiding grooves 488a, 488b. A channel 487c is included in the latch gate 487 for receiving the proximal end 498a of the trigger pin 498. A cavity and spring (both not shown) in the body 480 may also be included for receiving the proximal end 498a. A leaf spring 483 may be used to bias the latch gate 487 in a downward direction.

FIG. 12A shows the apparatus 401 in a second position, similar to the apparatus 301 shown in FIG. 10A. Prior to the second position, the apparatus 401 may have been provided initially in a first position, similar to the first position of the apparatus 301 shown in FIG. 9, or the apparatus 401 may be provided already in the second position. In the first and second positions, the compressed tamping spring 481 may bias the tamping device 485 into contact with the latch gate 487. In the second position, the cartridge 470 may be retracted proximally until the expandable member 446 is fully exposed distal to the distal end 474 and the locking bar 479a is extended into detent 436 in the pusher member 430.

In FIG. 12B, a snapshot of an instant in time illustrates a trigger point of the apparatus 401, similar to the trigger point of the previous embodiments. At the trigger point, the middle hub 476 may be coupled to the catheter hub 480. For example, the conical surfaces 477a, 477b may engage the centering surfaces 486 to align the middle hub 476 within the catheter hub 480 as the middle hub 476 enters the catheter hub 480. The middle hub 476 displaces the trigger pin 498 proximally until the intermediate member 498b is positioned in the channel 487c of the latch gate 487, thereby allowing the latch gate 487 to lower and the tamping device 485 to advance distally due to the force of the tamping spring 481. The latch gate 487 is lowered due to the bias of the leaf spring 483. During use, the expandable member 446 may be expanded and at least partially withdrawn similar to earlier embodiments until the expanded expandable member 446 substantially seals a body lumen from a puncture, thereby placing the sealant 402 within the puncture adjacent the body lumen.

Turning to FIG. 12C, the apparatus 401 is shown in a third position with the tamping device 485 fully displaced and the tamping spring 481 extended. The sealant 402 is compressed between the distal end 434 of the inner pusher member 430 and the expanded expandable member 446 (and/or tissue above the arteriotomy) due to the displacement of the tamping device 485 distally. Cooperating connectors (not shown) on the middle hub 476 and the distal end 484 of the body 480 may be used to couple the middle hub 476 to the catheter hub 480 upon activation, similar to the previous embodiments.

Figure 13:
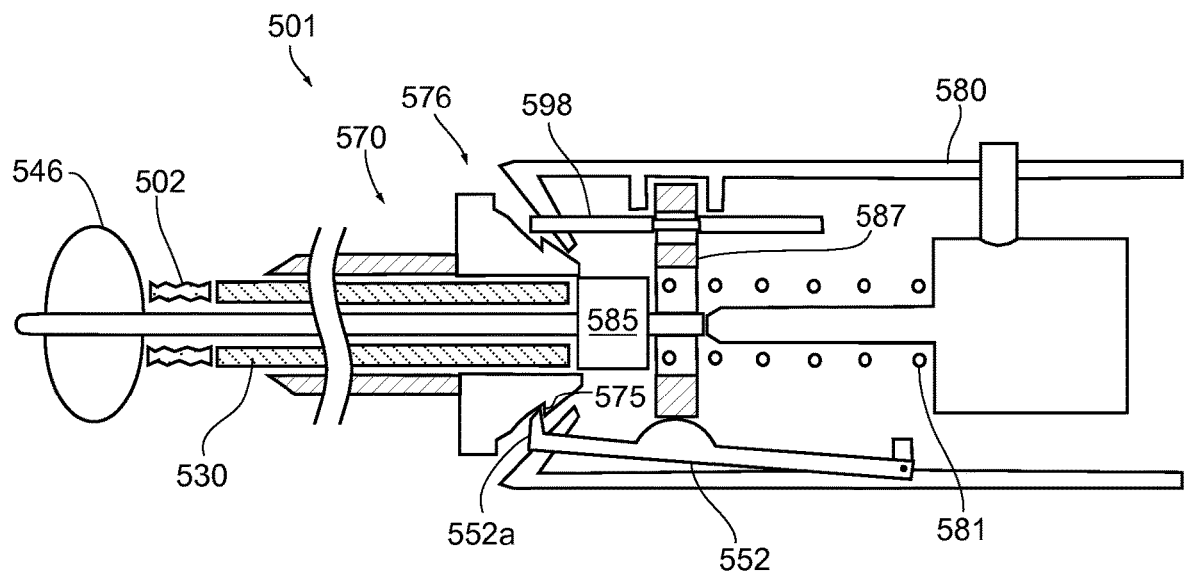
FIG. 13 is a cross-sectional view of another embodiment of an apparatus for delivering sealant into a puncture through tissue, including a tamping device in a position, similar to the embodiment shown in FIG. 11B.

Turning to FIG. 13, still another alternative embodiment of an apparatus 501 is shown for sealing a puncture similar to the apparatus 401 of FIGS. 12A-12C. The apparatus 501 includes a cartridge 570, and a catheter hub 580 similar to the previous embodiments. The apparatus 501 includes a hub latch 552 for displacing the latch gate 587. The hub latch 552 may include a leaf spring (not shown) for biasing the hub latch 552 in an upward direction, thereby displacing the latch gate 587 in an upward direction.

In FIG. 13, the apparatus 501 is shown in a third position similar to FIGS. 11B and 12C, where a tamping spring 581 is extended, similar to previous embodiments. Previously, the apparatus 501 may have been in an initial first position (not shown), and/or a second position (not shown), where the tamping spring 581 is compressed, also similar to the previous embodiments. In the third position, as shown, the middle hub 576 is fully mated with the catheter hub 580. Further, the trigger pin 598 is displaced proximally to release the latch gate 587 to be displaced upward by the raised hub latch 552, the hub latch 552 being raised by a leaf spring (not shown) or similar expanding device. The distal tip 552a of the raised hub latch 552 may be coupled to the latching detent 575 to secure the middle hub 576 to the catheter hub 580.

An expandable member 546 may be expanded and at least partially withdrawn similar to earlier embodiments until the expanded expandable member 546 substantially seals a body lumen from a puncture. A sealant 502 is compressed between the expanded expandable member 546 and an inner pusher member 530 affected by a full distal displacement of a tamping device 585 by the tamping spring 581.

Figure 14:
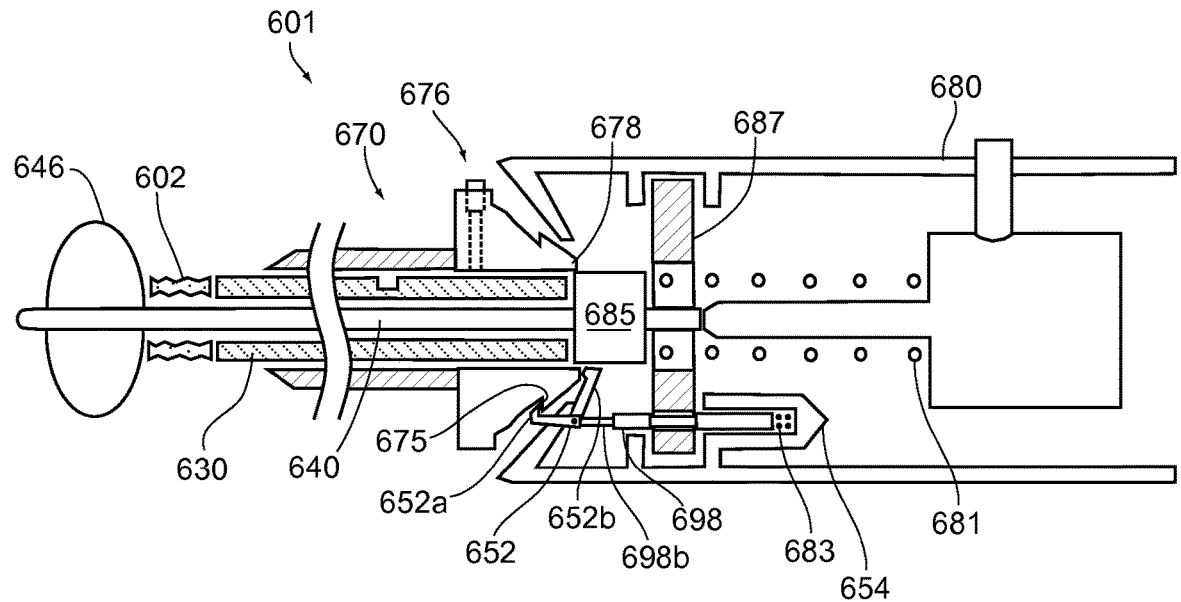
FIG. 14 is a cross-sectional view of yet another embodiment of an apparatus for delivering sealant into a puncture through tissue, including a tamping device in a position, similar to the embodiment shown in FIG. 11B.

Turning to FIG. 14, yet another alternative embodiment of an apparatus 601 is shown for sealing a puncture similar to the apparatus 401 of FIGS. 12A-12C. The apparatus 601 includes an elongate occlusion or positioning member 640, a cartridge 670, and a catheter hub 680, generally similar to the previous embodiments. The apparatus 601 may further include a hub latch 652 attached to a distal end 698b of a trigger pin 698. The hub latch 652 includes a first and second tip 652a, 652b. The trigger pin 698 includes a displacement spring 683 for biasing the trigger pin 698. The displacement spring 683 may be disposed within an enclosure 654 of the catheter hub 680.

The apparatus 601 is shown in a third position, where a tamping spring 681 is extended, similar to the previous embodiments. Previously, the apparatus 601 may have been in an initial first position, and/or a second position (neither shown), where the tamping spring 681 is compressed, similar to the previous embodiments. In the third position, a middle hub 676 is fully mated with the catheter hub 680. Further, the first tip 652a of hub latch 652 is mated with the latching detent 675 and the second tip 652b is displaced proximally by a proximal end 678 of the middle hub 676. The proximal displacement of the second tip 652b also proximally displaces the trigger pin 698 to release the latch gate 687, the latch gate 687 being biased upward by a leaf spring (not shown) or similar expanding member. The upwardly displaced latch gate 687 releases the tamping device 685 to be distally displaced by the tamping spring 681.

The expandable member 646 may be expanded and at least partially withdrawn similar to earlier embodiments until the expanded expandable member 646 substantially seals a body lumen from a puncture. The sealant 602 is compressed between the expanded expandable member 646 and the inner pusher member 630 affected by full distal displacement of a tamping device 685 by the tamping spring 681.

Figure 15A:
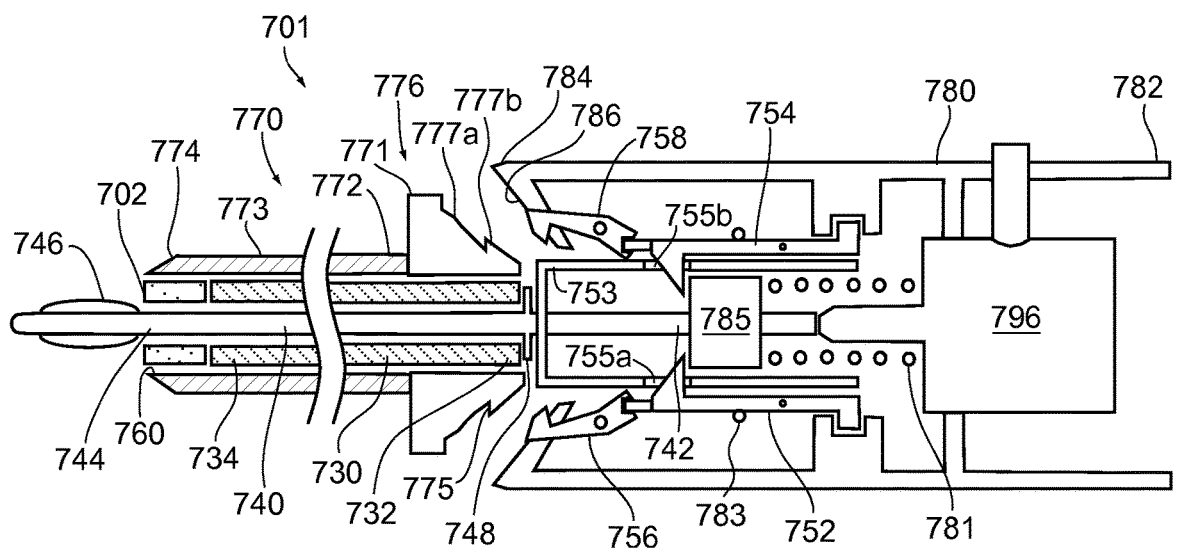
FIGS. 15A-15C are cross-sectional views of an apparatus for delivering a sealant device into a puncture through tissue including a tamping device employing complementary latches.
Figure 15B:
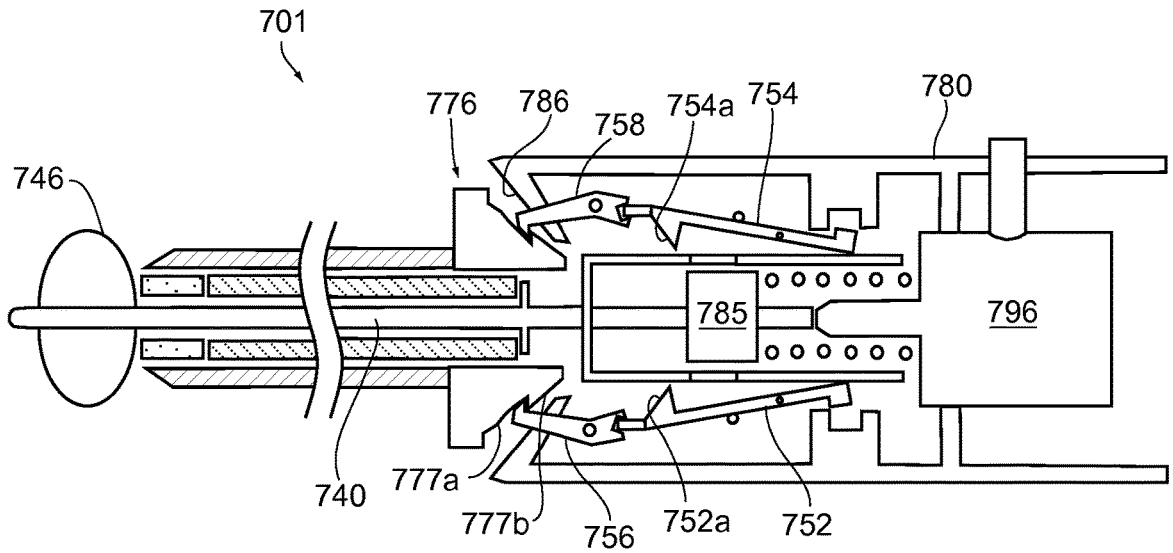
Figure 15C:
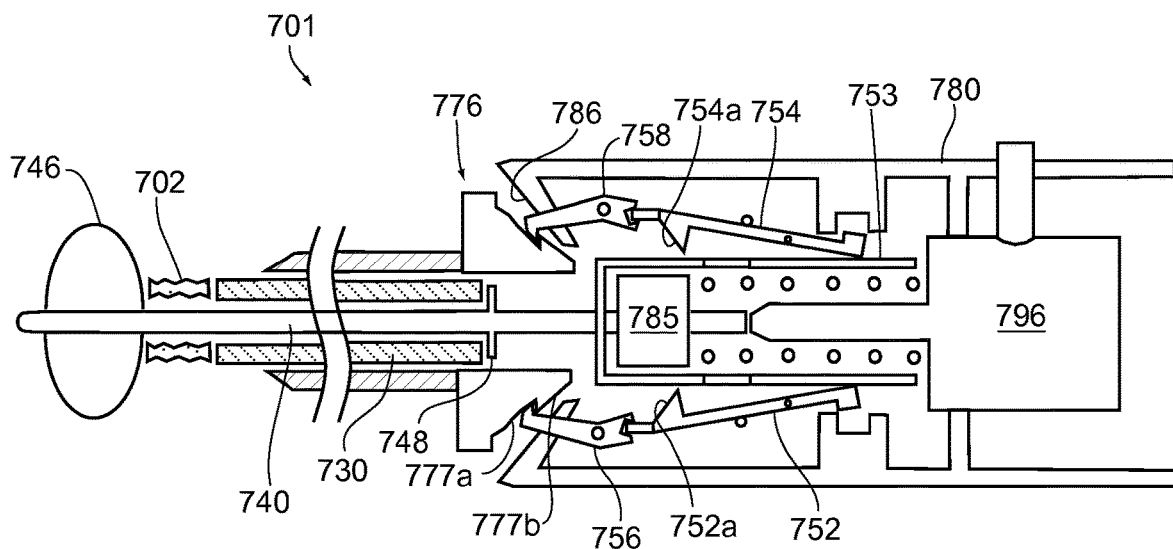

Turning now to FIG. 15A-15C, yet another embodiment of an apparatus 701 is shown for sealing a puncture. The apparatus 701 includes an elongate occlusion or positioning member 740, a cartridge 770, and a catheter hub 780. The positioning member 740 may be similar to those described elsewhere herein and includes a proximal end 742, a distal end 744, and an expandable member 746. Additionally, the positioning member 740 may include a ring 748 sized for displacing an inner pusher member 730, as described further below.

The cartridge 770 includes an outer tubular member 773, and a middle hub 776. The outer tubular member 773 includes a lumen 760 extending between a proximal end 772, and distal end 774 thereof. A sealant 702 and inner pusher member 730 are disposed within the outer tubular member 773. The inner pusher member 730 includes a lumen extending between a proximal and distal end 732, 734. The middle hub 776 is similar to previous embodiments and includes a main cylinder 771, first conical surface 777a, and second conical surface 777b. Included between the first and second conical surfaces 777a, 777b is a latching detent 775. The middle hub 776 may also include a pushbutton and a locking bar (both not shown) for cooperating with a detent (also not shown) in the inner pusher member 730, similar to the previous embodiments, e.g., to prevent proximal movement of the cartridge 770 until the pushbutton (not shown) is pressed. In addition or alternatively, the apparatus 701 may include a peel away lock (not shown) to prevent proximal movement of the cartridge 770.

The catheter hub 780 generally includes a body or outer housing 780 including proximal and distal ends 782, 784. The body 780 includes a balloon inflator 796, tamping device 785, and lower and upper tamping latches 752, 754. The body 780 may further include centering surfaces 786, lower and upper hub latches 756, 758, and carriage 753. A circular spring clip 783 is used to bias the lower and upper tamping latches 752, 754 in a radially inward direction. The carriage 753 includes lower and upper release slots 755a, 755b for displacing the tamping latches 752, 754 in an outward direction when the carriage 753 is displaced in a proximal direction. A tamping spring 781 is compressed between the tamping device 785 and the balloon inflator 796.

FIG. 15A shows the apparatus 701 in a second position. Prior to the second position, the apparatus 701 may have occupied a first position (not shown) similar to the first position described in previous embodiments. In the second position, the positioning member 740 is advanced distally until the expandable member 746 is fully exposed distal to the distal end 774. A pushbutton (not shown) and locking bar (not shown) may be used with a cooperating detent (not shown) on the inner pusher member 730, e.g., as described in the previous embodiments, to secure the apparatus 701 in the second position.

FIG. 15B is a snapshot of an instant in time illustrating a trigger point of the apparatus 701. As shown, at the trigger point, the middle hub 776 is coupled with the catheter hub 780, and the conical surfaces 777a, 777b have mated with the centering surfaces 786. The middle hub 776 has displaced the carriage 753 proximally thereby rotating the tamping latches 752, 754 outwardly away from the tamping device 785. The outwardly rotating tamping latches 752, 754 cause the proximal ends of hub latches 756, 758 to rotate downwardly to a latch position to mate with latching detents 775. The tamping device 785 is then free to release in the distal direction. The expandable member 746 may be expanded and at least partially withdrawn similar to earlier embodiments until the expanded expandable member 746 substantially seals a body lumen from a puncture.

Turning to FIG. 15C, the apparatus 701 is shown in the third position with the tamping device 785 fully displaced distally and the tamping spring 781 extended, thus compressing or tamping the sealant 702 between the inner pusher member 730 and the expanded expandable member 746. The displacement of the tamping device 785 forces the ring 748 to distally displace the inner pusher member 730. The middle hub 776 is secured to the catheter hub 780 by the downwardly rotated hub latches 756, 758, which are maintained in the latch position by the outwardly rotated tamping latches 752, 754. Distal tips 752a, 754a of tamping latches 752, 754 rest in contact with an outer surface of the carriage 753. Construction and operation of these embodiments generally proceed similar to one another.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the scope of the appended claims.

We claim:

1. An apparatus for sealing a puncture extending through tissue, comprising:
   an elongate member comprising a proximal end, a distal end sized for insertion into a puncture through tissue, and an expandable member on the distal end;
   a cartridge comprising a proximal end, a distal end sized for insertion into the puncture, and a lumen extending between the proximal and distal ends sized for receiving the elongate member therein;
   a sealant disposed within the cartridge lumen adjacent the cartridge distal end;
   a pusher member disposed within the cartridge lumen adjacent to the sealant; and
   a tamping device on the cartridge proximal end for biasing the pusher member distally relative to the sealant when activated, wherein the tamping device comprises a secondary pusher member and the elongate member comprises a catch for engaging a latch element on the secondary pusher member when the secondary pusher member is advanced distally beyond the catch.

2. The apparatus of claim 1, wherein the cartridge is movable along the elongate member from a proximal position wherein the cartridge is disposed adjacent the elongate member proximal end to a distal position wherein the sealant is disposed adjacent the expandable member and the tamping device is activated to bias the pusher member to move distally to push the sealant towards the expandable member.

3. The apparatus of claim 2, wherein the expandable member is expandable to an expanded state before the cartridge is advanced to the distal position such that the sealant is compressed between the pusher member and the expanded expandable member when the tamping device is activated.

4. The apparatus of claim 2, wherein the elongate member and pusher member comprise cooperating features that engage with one another when the cartridge is advanced to the distal position to prevent subsequent proximal movement of the pusher member relative to the elongate member.

5. The apparatus of claim 2, further comprising a cartridge hub on the cartridge proximal end for directing the cartridge from the proximal position to the distal position, the cartridge hub comprising the tamping device therein.

6. The apparatus of claim 5, wherein the cartridge hub is slidably coupled to the cartridge proximal end, the tamping device comprising a slider member within the cartridge hub fixedly coupled to the cartridge proximal end and a spring member coupled to a proximal end of the pusher member, the slider member biased to a first position within the cartridge hub such that the slider member moves distally with the cartridge hub when the cartridge is directed towards the distal position, but movable proximally within the cartridge hub to a second position when the cartridge is advanced to the distal position, thereby compressing the spring member to bias the pusher member to move distally.

7. The apparatus of claim 6, wherein the tamping device further comprises a support member fixed in the cartridge hub that is coupled to the pusher member when the cartridge is advanced to the distal position and the slider member moves to the second position, thereby engaging cooperating features on the pusher member and elongate member to prevent subsequent proximal movement of the pusher member relative to the elongate member.

8. The apparatus of claim 1, further comprising a marker on the elongate member for indicating that the tamping device is in an active position.

9. The apparatus of claim 1, wherein the tamping device comprises a tamping spring and an auto advance spring.

10. The apparatus of claim 9, wherein the tamping spring is coupled between the pusher member and a secondary pusher member.

11. The apparatus of claim 9, wherein the tamping spring is compressible between the pusher member and a secondary pusher member.

12. The apparatus of claim 1, wherein the tamping device comprises a spring for distally advancing the pusher member thereby compressing the sealant between the pusher member and the expandable member when the expandable member is expanded.

* * * * *